(12) United States Patent
Chow et al.

(10) Patent No.: US 8,472,022 B2
(45) Date of Patent: Jun. 25, 2013

(54) SPECTROSCOPIC DETECTION SYSTEM AND METHOD

(75) Inventors: Jong Hann Chow, Ainslie (AU); Malcolm Bruce Gray, Pennant Hills (AU); Ian Charles Murray Littler, Balmain (AU); David Ernest McClelland, O'Connor (AU)

(73) Assignee: The Australian National University (AU)

( * ) Notice: Subject to any disclaimer, the term of this patent is extended or adjusted under 35 U.S.C. 154(b) by 160 days.

(21) Appl. No.: 12/746,398

(22) PCT Filed: Dec. 5, 2008

(86) PCT No.: PCT/AU2008/001804
§ 371 (c)(1),
(2), (4) Date: Sep. 3, 2010

(87) PCT Pub. No.: WO2009/070849
PCT Pub. Date: Jun. 11, 2009

(65) Prior Publication Data
US 2010/0315642 A1 Dec. 16, 2010

(30) Foreign Application Priority Data
Dec. 5, 2007 (AU) ................................ 2007906639

(51) Int. Cl.
*G01N 21/00* (2006.01)
(52) U.S. Cl.
USPC ........................................................ 356/432
(58) Field of Classification Search
None
See application file for complete search history.

(56) References Cited

U.S. PATENT DOCUMENTS

| 4,058,725 | A | * | 11/1977 | Aine | ............................. 250/343 |
| 5,636,035 | A | | 6/1997 | Whittaker et al. | |
| 7,012,696 | B2 | * | 3/2006 | Orr et al. | ........................ 356/454 |

FOREIGN PATENT DOCUMENTS
GB 1248405 A 10/1971

OTHER PUBLICATIONS

McGarvey, Timothy, et al., "Finesse and Sensitivity Gain in Cavity-Enhanced Absorption Spectroscopy of Biomolecules in Solution;" 2006; Optics Express; vol. 14; No. 22; pp. 10441-10451.
Slagmolen, Bram J.J., Phase-Sensitive Reflection Technique for Characterization of a Fabry-Perot Interferometer; Jul. 20, 2000; Applied Optics; vol. 39; No. 21; pp. 3638-3643.
Vallance, C., "Innovations in Cavity Ringdown Spectroscopy;" 2005; New Journal of Chemistry; vol. 29; pp. 867-864.

(Continued)

*Primary Examiner* — Tu Nguyen
(74) *Attorney, Agent, or Firm* — Kilpatrick Townsend & Stockton LLP

(57) ABSTRACT

A system and method for spectroscopic detection of loss in a resonator cavity is disclosed. The system can include a number of components. A tunable laser source can generate a laser beam. A frequency locking system can lock the frequency of the laser beam to a resonance of the resonator cavity or lock the length of the cavity to the frequency of the laser beam. The first modulation element can modulate the laser beam at a first modulation frequency to generate a modulated laser beam. The input coupler can direct the modulated laser beam into the resonator cavity. The first directing element can direct a first portion of light reflected from the input coupler to a first photodetector. The first demodulator can demodulate the first modulation signal to generate a first error signal which is a function of the loss in the resonator cavity.

26 Claims, 16 Drawing Sheets

OTHER PUBLICATIONS

Ye, J., et al, "Ultrasensitive Detections in Atomic and Molecular Physics: Demonstration in Molecular Overtone Spectroscopy;" Jan. 1998; Journal of the Optic Society of America B; vol. 15; No. 1; pp. 6-15.

Chow, J., et al., "Using Active Resonator Impedance Matching for Shot-Noise Limited, Cavity Enhanced Amplitude Modulated Laser Absorption Spectroscopy;" May 26, 2008; Optics Express; vol. 16; No. 11; pp. 7726-7738.

Schmidt, F., "Laser-Based Absorption Spectrometry: Development of NICE-OHMS Towards Ultra-Sensitive Trace Species Detection;" Nov. 2007; Doctoral Thesis; Umea University; Abstract from Internet; 3 pages; http://www/diva-portal.org/umu/abstract.

Paldus, Barbara A., "An Historical Overview of Cavity-Enhanced Methods;" 2005; Canadian Journal of Physics; vol. 83; pp. 975-999.

Taubman, M. et al., "Long Wave Infrared Cavity Enhanced Sensors;" Oct. 2004; Pacific-Northwest National Laboratory; PNNL-15103; Retrieved from Internet; http://www.pnl.gov/main/publications/external/technical_reports.

Black, E.D.; "An introduction to Pound-Drever-Hall laser frequency stabilization"; *Am. J. Phys.*; 69(1):79-87 (Jan. 2001).

* cited by examiner

SPECTROSCOPIC DETECTION SYSTEM AND METHOD

CROSS-REFERENCE TO RELATED APPLICATIONS

This application is the US National Stage entry under §371 of International Application No. PCT/AU2008/001804, filed Dec. 5, 2008, which claims benefit of Australian Application No. 2007906639, filed Dec. 5, 2007; the disclosures of each are hereby incorporated by reference.

TECHNICAL FIELD

The present invention relates to methods and apparatus for optical absorption spectroscopy and in particular to shot nose limited optical absorption spectroscopy methods and apparatus.

The invention has been developed primarily for use as a method and associated apparatus for optical spectroscopy using a cavity enhanced amplitude modulated detection method for shot noise limited detection thresholds and will be described hereinafter with reference to this application. However, it will be appreciated that the invention is not limited to this particular field of use.

BACKGROUND OF THE INVENTION

Any discussion of the background art throughout the specification should in no way be considered as an admission that such background art is prior art, nor that such background art is widely known or forms part of the common general knowledge in the field.

Optical absorption spectroscopy is an active branch of research which finds important applications in biochemical sensing. The fundamental challenge is to attain ever lower detection thresholds. Towards this end, optical resonators are excellent transducers for amplifying the effects of small optical absorption and loss.

By comparing the intensity of an optical beam before and after the beam is passed through a substance, the optical density or absorption of that substance can be determined. Shot noise on the measurement beam sets the ultimate resolution limit to which this measurement can be made.

Methodologies adopting radio-frequency modulation for detecting vibrational overtones of gas-phase molecules have recorded shot-noise limited performance at $1.5 \times 10^{-13}/\sqrt{Hz}$ [see for example J. Ye, L. S. Ma and J. L. Hall, *Ultrasensitive detections in atomic and molecular physics: demonstration in molecular overtone spectroscopy*, J. Opt. Soc. Am. B, 15, p. 615 (1998)]. These frequency modulation (FM) spectroscopy techniques are powerful for species with absorption linewidths of ~1 GHz.

For molecules in liquids, on the other hand, the spectral line is greatly broadened with a homogeneous profile. This can be compounded by overlapping of profiles from different spectral lines, resulting in an absorption continuum which can extend up to tens of THz. With conventional laser modulation technology, this absorption continuum appears as a broadband loss to the spectral components of the frequency modulated laser, which renders frequency modulation spectroscopy techniques (such as those described by J. Ye et. al. referenced above) ineffective.

The most widely investigated cavity enhanced technique suitable for broadband loss is time-domain ring-down spectroscopy. However, this technique typically yields poor sensitivity due to limited optical duty cycle and large effective noise bandwidth.

A highly sensitive alternative for measuring absorption in liquids has recently been proposed [see Timothy McGarvey, Andre Conjusteau and Hideo Mabuchi, *Finesse and sensitivity gain in cavity-enhanced absorption spectroscopy of biomolecules in solution*, Opt. Ex., 14, 22, 10441-10451 (2006)] where the laser is locked on resonance, while the reflected power is continually monitored for changes in cavity loss. The sensitivity achieved, however, was still greater than 200 times the shot noise limit.

It is an object of the present invention to substantially overcome or at least ameliorate one or more of the above disadvantages, or at least to provide a useful alternative.

SUMMARY OF THE INVENTION

In the claims of this application and in the description of the invention, except where the context requires otherwise due to express language or necessary implication, the term "comprise" or variations such as "comprises" or "comprising" is used in an inclusive sense, i.e. to specify the presence of the stated features but not to preclude the presence or addition of further features in various embodiments of the invention. As used herein, the singular forms "a", "an", and "the" include the corresponding plural reference unless the context clearly dictates otherwise. Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

Throughout the specification, the term "impedance matching" refers to the suppression of reflected radiation at a particular frequency from an interface, in particular, the optical interface to a resonator cavity. The terms "impedance matched state" and "impedance matching condition" refer to the state of an optical resonator which is impedance matched.

Described herein are methods and apparatus for shot noise or near shot noise limited detection performance in a spectroscopy technique using a cavity enhanced amplitude modulated laser absorption spectroscopy (CEAMLAS) technique. Arrangements of the method comprise amplitude modulation (AM) interferometry for absorption measurements while the laser is resonant with the cavity. For optimum performance, the measurements are performed in closed-loop operation with active impedance matching of a resonator cavity and frequency locking between the laser and cavity, to ensure a large dynamic range with optimum sensitivity limit, while facilitating a measurement which is immune to the laser intensity noise.

Exemplary arrangements of apparatus for carrying out the cavity enhanced method are described herein in both free-space and optical fibre guided wave architecture, although it will be appreciated by the skilled addressee that the method may also be performed in other optical architecture arrangements such as waveguide guided wave systems, or systems comprising elements from any combination of free-space, optical fibre, waveguide or other guided wave systems (for example photonic crystal elements).

According to a first aspect, there is provided a system for spectroscopic detection of a loss in a resonator cavity. The system may comprise a tunable laser source for generating a laser beam. A frequency locking system for either locking the frequency of the laser beam to a resonance of the resonator cavity or locking the length of the cavity to the frequency of the laser beam may also provided. A first modulation element may modulate the laser beam at a first modulation frequency to generate a modulated laser beam. An input coupler may be used to direct the modulated laser beam into the resonator cavity. A first portion of light reflected from the input coupler may be directed by a first directing element such as a beamsplitter to a first photodetector to generate a first detected signal proportional to the amount of reflected light incident on the photodetector. A first demodulator capable of demodulating the first modulation signal from the first detected signal may be provided in order to generate a first error signal which is a function of the loss in the resonator cavity at the frequency $\omega_o$ of the laser beam. The resonator cavity may comprise a variable coupler and the system may further comprise a first actuator for varying the reflectivity of the variable coupler in response to the first error signal to maintain the resonator cavity in an impedance matched state via a high gain negative feedback loop. The first detected signal may be detected with a detector and the first error signal determined from the first detected signal to determine the loss in the resonator cavity at the optical frequency $\omega_o$ of the laser.

In an exemplary arrangement of the first aspect, the system for spectroscopic detection of a loss in a resonator cavity comprises: a tunable laser source for generating a laser beam; means for either locking the frequency of the laser beam to a resonance of the resonator cavity or locking the length of the cavity to the frequency of the laser beam; a first modulation element for modulating the laser beam at a first modulation frequency to generate a modulated laser beam; an input coupler adapted for directing the modulated laser beam into the resonator cavity; a first directing element for directing a first portion of light reflected from the input coupler to a first photodetector to generate a first detected signal; and a first demodulator capable of demodulating the first modulation signal from the first detected signal to generate a first error signal which is a function of the loss in the resonator cavity.

In a further exemplary arrangement of the first aspect, the resonator cavity may comprise a variable coupler and the system may further comprise a first actuator for varying the reflectivity of the variable coupler in response to the first error signal to maintain the resonator cavity in an impedance matched state. The system may also comprise a detector for detecting the first error signal to determine the loss in the resonator cavity at the frequency of the laser. The first modulator may be an amplitude modulator and the first error signal may be an amplitude modulated error signal. The input coupler may the variable coupler. In other arrangements the variable coupler may be an output coupler of the resonator cavity, or may be disposed within the resonator cavity. The resonator cavity may be a linear cavity or a ring cavity and may be either a free-space cavity or a guided wave cavity. Where the resonator cavity is a guided wave cavity the cavity may be an optical fibre cavity. The first directing element may be a beamsplitter. The modulator may not necessarily produce a pure amplitude modulation of the laser beam, instead the modulator may be adapted to provide a frequency or phase modulation of the laser beam which, as a consequence of modulating the frequency and/or phase of the laser beam a, component of amplitude modulation is introduced onto the laser beam. For example, the laser may be a diode laser and the modulator may modulate the operating current of the diode laser to introduce a predominant phase modulation (which is equivalent to a frequency modulation) and a parasitic amplitude modulation on to the laser beam from the diode laser. The parasitic amplitude modulation may then be used to generate the first error signal.

A frequency locking system of the arrangements of the first aspect may comprise: a second modulation element for modulating the laser beam at a second modulation frequency such that the modulated beam would comprise modulated components at both the first and the second modulation frequencies and the detected signal comprises components of both first and second modulation signals; a second demodulator for demodulating the second modulation signal from the second detected signal to generate a second error signal; and a second actuator for maintaining the frequency of the laser beam at resonance with the cavity in response to the second error signal. The second actuator may be adapted for tuning the frequency of the laser beam in response to the second error signal to lock the laser output to a resonance frequency of the cavity. Alternatively, the second actuator may be adapted for tuning the length of the resonator cavity in response to the second error signal to lock the cavity resonance to the carrier frequency of the laser output. The frequency locking system may further comprise a second directing element for directing a second portion of light reflected from the variable input coupler to a second detector to generate a second detected signal wherein the second demodulator is adapted for demodulating the second modulation signal from the second detected signal to generate the second error signal. The second modulator may be a phase modulator and the second error signal may be a phase modulated error signal. The phase modulator may be an electro-optic modulator. The second modulator may be selected from the group of a phase modulator, a frequency modulator, a current modulator, or a phase modulator which also causes an amplitude modulation. The second directing element may be a beamsplitter, although in other arrangements, it will be appreciated that the directing element may not be required. The frequency locking system may be a Pound-Drever-Hall frequency locking system.

The resonator cavity may be a high finesse resonator cavity and the finesse of the high finesse resonator cavity may be greater than 50, greater than 100, greater than 1000 and may be in the range of 50 to 100, 50 to 150, 50 to 200, 50 to 500, 50 to 1000, 50 to 500, 50 to 10,000, 50 to 50,000, 70 to 100, 70 to 150, 70 to 200, 70 to 500, 70, to 1000, 70 to 10,000, 100 to 150, 100 to 200, 100 to 500, 100 to 1000, 100 to 10,000, or 100 to 50,000.

Where the cavity is a free space cavity, the variable coupler may comprise: first and second reflectors spaced apart from each other; and an actuator to vary the position of the first reflector thereby to vary the spacing between the first and second reflectors and thus vary the effective reflectivity of the variable coupler. The reflectivity of each of the first and second reflectors may be in the range of about 50% to about 99.99% or about 60% to 99%. The effective reflectivity of the variable coupler may be capable of being varied between about 20% and about 99.99%. The variable coupler may be a variable reflectivity Fabry Perot interferometer. In other arrangements, the variable coupler may be a variable frustrated total internal reflection element or other variable evanescent wave coupling element. The variable coupler may be either an input or an output coupler of the resonator cavity. In other arrangements, the variable coupler may be disposed within the resonator cavity.

Where the resonator cavity is a guided wave resonator cavity, the variable coupler may comprise: first and second guided wave portions, the first guided wave portion forming part of the resonator cavity and the second guided wave portion in optical communication with the laser source; and an actuator to vary the optical coupling ratio between the first and second guided wave portions. The optical coupling ratio between the first and second guided wave portions may be capable of being varied between about 0% and about 100%.

According to a second aspect, there is provided a spectroscopic detection method for detecting of a loss in a resonator cavity. The method may comprise generating a laser beam at a frequency $\omega_o$ using a tunable laser source. The frequency of the laser beam may either be locked to a resonance of the resonator cavity or the length of the cavity may be locked to the frequency of the laser beam. The laser beam may be modulated at a first modulation frequency to generate a modulated laser beam using a first modulation element. The modulated laser beam may be directed into the resonator cavity via a suitable input coupler. A first portion of light reflected from the input coupler may be directed to a first photodetector to generate a first detected signal. The first modulation signal from the first detected signal may be demodulated using a first demodulator to generate a first error signal. The resonator cavity may comprise a variable coupler and the method may further comprise varying the reflectivity of the variable coupler using a first actuator in response to the first error signal to maintain the resonator cavity in an impedance matched state. The first error signal may also be detected to provide a measure of the magnitude of loss in the resonator cavity.

In an exemplary arrangement of the second aspect, there is provided a spectroscopic detection method for detecting of a loss in a resonator cavity, the method comprising: generating a laser beam at a frequency $\omega_o$ using a tunable laser source; locking the frequency of the laser beam to a resonance of the resonator cavity; modulating the laser beam at a first modulation frequency to generate a modulated laser beam with a first modulation element; directing the modulated laser beam into the resonator cavity via a suitable input coupler; directing a first portion of light reflected from the input coupler to a first photodetector to generate a first detected signal; demodulating the first modulation signal from the first detected signal using a first demodulator to generate a first error signal which is a function of the loss in the resonator cavity.

In a further exemplary arrangement of the second aspect, the resonator cavity may comprise a variable coupler and the method may further comprise using a first actuator to vary the reflectivity of the variable coupler in response to the first error signal to maintain the resonator cavity in an impedance matched state. The first error signal may be detected in either an open loop arrangement without actuation of the variable coupler or in a closed loop arrangement with actuation of the variable coupler to maintain the resonator in an impedance matched state thereby to provide a measure of the magnitude of loss in the resonator cavity. The first modulator may be an amplitude modulator and the modulated laser beam may be an amplitude modulated laser beam.

The step of locking the frequency of the laser beam to a resonance of the resonator cavity may comprise: modulating the laser beam at a second modulation frequency using a second modulation element such that the modulated beam comprises first and second modulated signals at both the first and the second modulation frequencies and the detected signal comprises components of both the first and the second modulation signals; demodulating the second modulation signal from the detected signal using a second demodulator to generate a second error signal; and using a second actuator, maintaining the frequency of the laser beam at resonance with the cavity in response to the second error signal. The second actuator may be adapted for tuning the frequency of the laser beam in response to the second error signal to lock the laser output to a resonance frequency of the cavity. Alternatively, the second actuator may be adapted for tuning the length of the resonator cavity in response to the second error signal to lock the cavity resonance to the carrier frequency of the laser output. In an alternate arrangement, a second portion of the light reflected from the input coupler may be directed to a second photodetector to generate a second detected signal comprising the second modulation signal and the method comprises demodulating the second modulation signal from the second detected signal to generate the second error signal. The step of locking the frequency of the laser beam to a resonance of the resonator cavity may comprise a Pound-Drever-Hall frequency locking method.

According to a third aspect, there is provided a spectroscopic detection method for detecting of a loss in a resonator cavity. The method may comprise the step of providing a tunable laser beam. The method may further comprise the step of: either maintaining the carrier frequency of the laser beam to be on resonance with a mode of the resonator; or locking the length of the cavity to the frequency of the laser beam; or both. The method may further comprise the step of modulating the laser beam with an amplitude modulation to generate an amplitude modulated laser beam. The method may further comprise the step of resonating the laser carrier within the resonator cavity. The method may further comprise the step of detecting reflected amplitude modulated light from the resonator cavity at the frequency of the laser beam. The method may further comprise the step of generating a first error signal from the amplitude modulated light reflected from the cavity. The first error signal may be a function of the loss in the resonator cavity.

According to an exemplary arrangement of the third aspect, there is provided a spectroscopic detection method for detecting of a loss in a resonator cavity comprising the steps of: providing a tunable laser beam; either maintaining the carrier frequency of the laser beam to be on resonance with a mode of the resonator or locking the length of the cavity to the frequency of the laser beam; modulating the laser beam with an amplitude modulation to generate an amplitude modulated laser beam; resonating the laser carrier within the resonator cavity; detecting reflected amplitude modulated light from the resonator cavity at the frequency of the laser beam; and generating a first error signal from the amplitude modulated light reflected from the cavity, wherein the first error signal may be a function of the loss in the resonator cavity.

According to a fourth aspect there is provided a method for placing a resonator cavity in an impedance matched state. The method may comprise the step of providing a tunable laser beam. The method may further comprise the step of either: maintaining the carrier frequency of the laser beam to be on resonance with a mode of the resonator; or locking the length of the cavity to the frequency of the laser beam; or both. The method may further comprise the step of modulating the laser beam with an amplitude modulation to generate an amplitude modulated laser beam. The method may further comprise the step of resonating the laser carrier within the resonator cavity. The method may further comprise the step of detecting reflected amplitude modulated light from the resonator cavity at the frequency of the laser beam. The method may further comprise the step of generating a first error signal from the amplitude modulated light reflected from the cavity. The first error signal may be a function of the loss in the resonator cavity. The method may further comprise the step of actuating a suitable reflector of the resonator cavity to place the resonator in an impedance matched state in response to the first error signal or a signal derived therefrom.

According to an exemplary arrangement of the fourth aspect there is provided a method for placing a resonator cavity in an impedance matched state comprising the steps of: providing a tunable laser beam; either maintaining the carrier frequency of the laser beam to be on resonance with a mode of the resonator or locking the length of the cavity to the frequency of the laser beam; modulating the laser beam with an amplitude modulation to generate an amplitude modulated laser beam; resonating the laser carrier within the resonator cavity; detecting reflected amplitude modulated light from the resonator cavity at the frequency of the laser beam; generating a first error signal from the amplitude modulated light reflected from the cavity, wherein the first error signal may be a function of the loss in the resonator cavity; and in response to the first error signal or a signal derived therefrom, actuating a suitable reflector of the resonator cavity to place the resonator in an impedance matched state.

According to a fifth aspect, there is provided a system for placing a resonator cavity in an impedance matched state. The system may comprise a tunable laser source for generating a laser beam. The system may further comprise a locker for either: locking the frequency of the laser beam to a resonance of the resonator cavity: or locking the length of the cavity to the frequency of the laser beam; or both. The system may further comprise a first modulation element for modulating the laser beam at a first modulation frequency to generate a modulated laser beam. The system may further comprise an input coupler adapted for directing the modulated laser beam into the resonator cavity. The system may further comprise a first directing element for directing a first portion of light reflected from the input coupler to a first photodetector to generate a first detected signal. The system may further comprise a first demodulator capable of demodulating the first modulation signal from the first detected signal to generate a first error signal. The first error signal may be a function of the loss in the resonator cavity. The system may further comprise an actuator for actuating a suitable reflector of the resonator cavity to place the resonator in an impedance matched state in response to the first error signal or a signal derived therefrom.

According to an exemplary arrangement of the fifth aspect, there is provided a system for placing a resonator cavity in an impedance matched state comprising: a tunable laser source for generating a laser beam; means for either locking the frequency of the laser beam to a resonance of the resonator cavity or locking the length of the cavity to the frequency of the laser beam; a first modulation element for modulating the laser beam at a first modulation frequency to generate a modulated laser beam; an input coupler adapted for directing the modulated laser beam into the resonator cavity; a first directing element for directing a first portion of light reflected from the input coupler to a first photodetector to generate a first detected signal; a first demodulator capable of demodulating the first modulation signal from the first detected signal to generate a first error signal which is a function of the loss in the resonator cavity; and means for actuating a suitable reflector of the resonator cavity to place the resonator in an impedance matched state in response to the first error signal or a signal derived therefrom.

According to a sixth aspect, there is provided a method of determining a parameter, or a change in a parameter, of a material (either gaseous, liquid or solid) which causes a loss in a resonator cavity. The method may comprise the step of providing a tunable laser beam. The method may further comprise the step of either: maintaining the carrier frequency of the laser beam to be on resonance with a mode of the resonator or locking the length of the cavity to the frequency of the laser beam; or both. The method may further comprise the step of modulating the laser beam with an amplitude modulation to generate an amplitude modulated laser beam. The method may further comprise the step of resonating the laser carrier within the resonator cavity. The method may further comprise the step of detecting reflected amplitude modulated light from the resonator cavity at the frequency of the laser beam. The method may further comprise the step of generating a first error signal from the amplitude modulated light reflected from the cavity. The first error signal may be a function of the loss in the resonator cavity. The method may further comprise the step of determining the parameter and/or the change in the parameter from the first error signal. The step of determining the parameter and/or the change in the parameter from the first error signal may comprise calculating the parameter and/or the change in the parameter from the first error signal.

According to an exemplary arrangement of the sixth aspect, there is provided a method of determining a parameter, or a change in a parameter, of a material (either gaseous, liquid or solid) which causes a loss in a resonator cavity comprising the steps of: providing a tunable laser beam; either maintaining the carrier frequency of the laser beam to be on resonance with a mode of the resonator or locking the length of the cavity to the frequency of the laser beam; modulating the laser beam with an amplitude modulation to generate an amplitude modulated laser beam; resonating the laser carrier within the resonator cavity; detecting reflected amplitude modulated light from the resonator cavity at the frequency of the laser beam; generating a first error signal from the amplitude modulated light reflected from the cavity, wherein the first error signal may be a function of the loss in the resonator cavity; and determining the parameter and/or the change in the parameter from the first error signal. The step of determining the parameter and/or the change in the parameter from the first error signal may comprise calculating the parameter and/or the change in the parameter from the first error signal.

According to a seventh aspect, there is provided a system for determining a parameter, or a change in a parameter, of a material (either gaseous, liquid or solid) which causes a loss in a resonator cavity. The system may comprise a tunable laser source for generating a laser beam. The system may further comprise a locker for either: locking the frequency of the laser beam to a resonance of the resonator cavity: or locking the length of the cavity to the frequency of the laser beam; or both. The system may further comprise a first modulation element for modulating the laser beam at a first modulation frequency to generate a modulated laser beam. The system may further comprise an input coupler adapted for directing the modulated laser beam into the resonator cavity. The system may further comprise a first directing element for directing a first portion of light reflected from the input coupler to a first photodetector to generate a first detected signal. The system may further comprise a first demodulator capable of demodulating the first modulation signal from the first detected signal to generate a first error signal which is a function of the loss in the resonator cavity. The system may further comprise and a determiner for determining the parameter and/or the change in the parameter from the first error signal. The determiner may comprise a calculator, a computer or some other means. The determiner may be coupled to the first demodulator by a digital-to-analogue or a analogue-to-digital converter as necessary.

According to an exemplary arrangement of the seventh aspect, there is provided a system for determining a parameter, or a change in a parameter, of a material (either gaseous, liquid or solid) which causes a loss in a resonator cavity comprising: a tunable laser source for generating a laser beam; means for either locking the frequency of the laser beam to a resonance of the resonator cavity or locking the length of the cavity to the frequency of the laser beam; a first modulation element for modulating the laser beam at a first modulation frequency to generate a modulated laser beam; an input coupler adapted for directing the modulated laser beam into the resonator cavity; a first directing element for directing a first portion of light reflected from the input coupler to a first photodetector to generate a first detected signal; a first demodulator capable of demodulating the first modulation signal from the first detected signal to generate a first error signal which is a function of the loss in the resonator cavity; and means for determining the parameter and/or the change in the parameter from the first error signal. The means for determining either the parameter and/or the change in the parameter from the error signal may comprise a calculator, a computer or some other means. The means for determining may be coupled to the first demodulator by a digital-to-analogue or a analogue-to-digital converter as necessary.

In the fourth and sixth aspects the step of locking the frequency of the laser beam to a resonance of the resonator cavity may comprise: modulating the laser beam at a second modulation frequency using a second modulation element such that the modulated beam comprises first and second modulated signals at both the first and the second modulation frequencies and the detected signal comprises components of both the first and the second modulation signals; demodulating the second modulation signal from the detected signal using a second demodulator to generate a second error signal; and using a second actuator, maintaining the frequency of the laser beam at resonance with the cavity in response to the second error signal. The second actuator may be adapted for tuning the frequency of the laser beam in response to the second error signal to lock the laser output to a resonance frequency of the cavity. Alternatively, the second actuator may be adapted for tuning the length of the resonator cavity in response to the second error signal to lock the cavity resonance to the carrier frequency of the laser output. In an alternate arrangement, a second portion of the light reflected from the input coupler may be directed to a second photodetector to generate a second detected signal comprising the second modulation signal and the method comprises demodulating the second modulation signal from the second detected signal to generate the second error signal. The step of locking the frequency of the laser beam to a resonance of the resonator cavity may comprise a Pound-Drever-Hall frequency locking method.

A frequency locking system of the arrangements of the fifth and seventh aspects may comprise: a second modulation element for modulating the laser beam at a second modulation frequency such that the modulated beam would comprise modulated components at both the first and the second modulation frequencies and the detected signal comprises components of both first and second modulation signals; a second demodulator for demodulating the second modulation signal from the second detected signal to generate a second error signal; and a second actuator for maintaining the frequency of the laser beam at resonance with the cavity in response to the second error signal. The second actuator may be adapted for tuning the frequency of the laser beam in response to the second error signal to lock the laser output to a resonance frequency of the cavity. Alternatively, the second actuator may be adapted for tuning the length of the resonator cavity in response to the second error signal to lock the cavity resonance to the carrier frequency of the laser output. The frequency locking system may further comprise a second directing element for directing a second portion of light reflected from the variable input coupler to a second detector to generate a second detected signal wherein the second demodulator is adapted for demodulating the second modulation signal from the second detected signal to generate the second error signal. The second modulator may be a phase modulator and the second error signal may be a phase modulated error signal. The phase modulator may be an electro-optic modulator. The second modulator may be selected from the group of a phase modulator, a frequency modulator, a current modulator, or a phase modulator which also causes an amplitude modulation. The second directing element may be a beamsplitter, although in other arrangements, it will be appreciated that the directing element may not be required. The frequency locking system may be a Pound-Drever-Hall frequency locking system.

BRIEF DESCRIPTION OF THE DRAWINGS

Arrangements of the cavity enhanced amplitude modulated laser absorption spectroscopy method and arrangements of suitable apparatus for carrying out the method will now be described, by way of an example only, with reference to the accompanying drawings wherein:

FIG. 4A shows an example arrangement using separate detectors for each of the control loops, and FIG. 4B an alternate arrangement using a single photodetector detector, the output of which is used to obtain the error signal for both the phase-modulated frequency locking control loop and the amplitude modulated impedance matching control loop;

DETAILED DESCRIPTION OF THE PREFERRED EMBODIMENTS

Figure 1A:
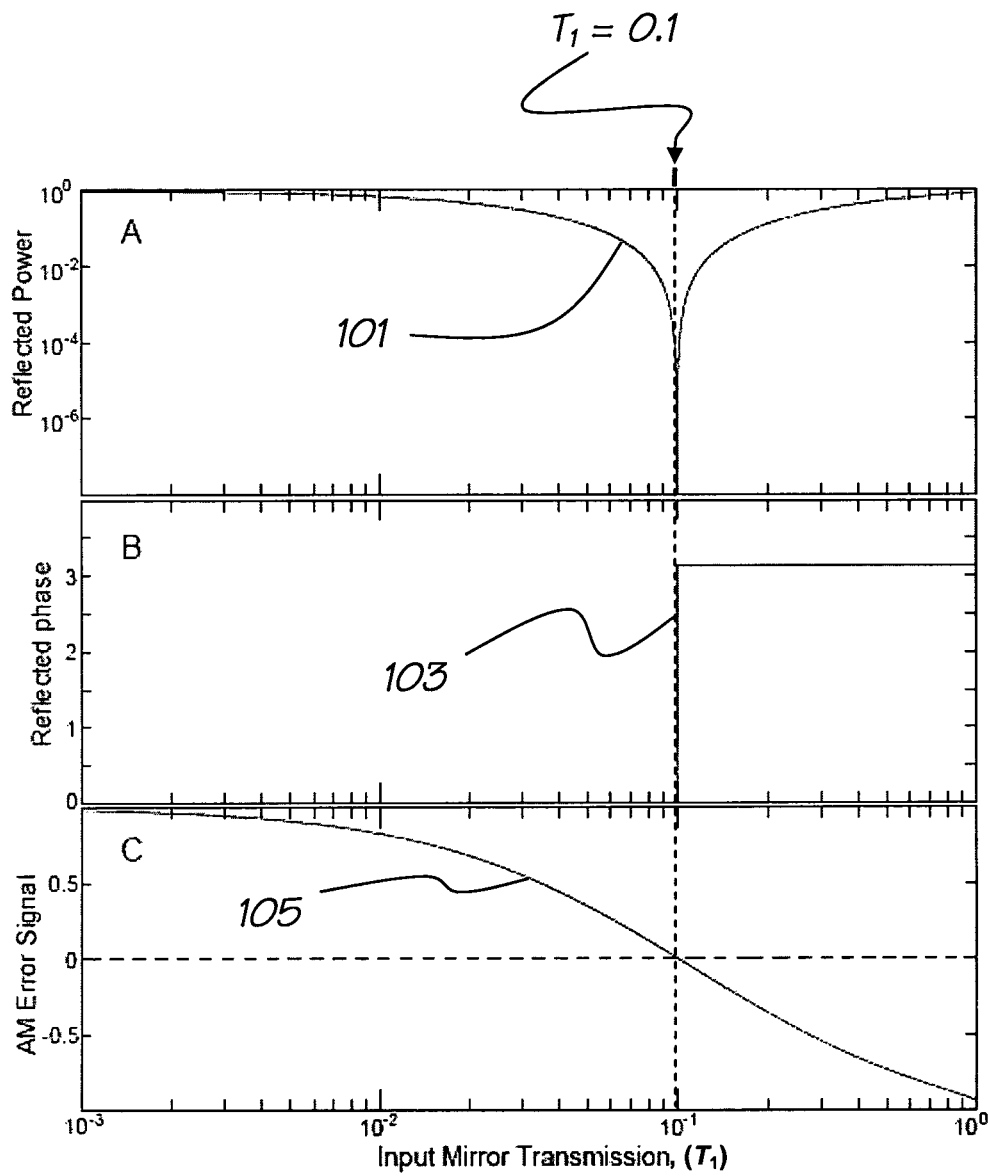
FIG. 1A is a graph showing three plots respectively describing: top—the normalised reflected power; middle—the optical phase of the reflected field from the resonator cavity: and bottom—the AM impedance matching error signal about a cavity resonance in the arrangements described herein.

Described herein is a method and associated apparatus for optical spectroscopy using a cavity enhanced amplitude modulated detection method for shot noise or near shot noise limited detection thresholds. In general terms, an amplitude modulated laser beam with a carrier frequency $\omega_o$ is held on resonance with an optical resonator cavity containing a loss mechanism and the reflected amplitude modulated light from the resonator cavity is used to determine the magnitude of the loss mechanism in the cavity at the carrier frequency $\omega_o$. The methods and apparatus for achieving this are described below and it will be seen by examples that the disclosed method is capable of providing shot noise limited detection of the loss in the resonator cavity.

In the absence of excess technical laser intensity noise, the fundamental sensitivity limit for a typical laser spectroscopy measurement technique and system is given by the shot-noise-limited relative intensity noise ($RIN_{shot}$) of the measurement. For an arrangement where an amount of substance is aimed to be detected in a single pass (i.e. the laser beam only interacts with the substance once) the $RIN_{shot}$ is expressed in terms of the sensitivity of the photodetector used in the system and the amount of optical power detected by the relation $$RIN_{shot} = \sqrt{\frac{2e}{\eta P_{opt}}} \quad (1)$$

where e is the electronic charge, $\eta$ is the photodetector responsivity in Amps/Watt and $P_{opt}$ is the optical power detected by the photodetector.

Placing the measurement within an optical resonator forces the incident light beam to transit through the substance to be measured many times and therefore the single pass absorption is amplified. This improves the shot noise limited absorption measurement to give $$RIN_{shot} = (\alpha l)_{SN} = \frac{\pi}{2F} \cdot \sqrt{\frac{2e}{\eta P_{opt}}} \quad (2)$$

where $$N_{bounce} = \frac{2F}{\pi} \quad (3)$$

to is the effective bounce number of the resonator, a is the absorption coefficient (in units of $cm^{-1}$); l is the sample length; $2F/\pi$ is the effective bounce number of the resonator; F is the cavity finesse; is the photodetector responsivity and $P_{op}$, is the optical power incident on the optical resonator. Hence, from Equations 2 and 3, the sensitivity of the attenuation measurement can be improved beyond the shot noise limit of the measurement beam by increasing the effective bounce number of the resonator i.e. increasing the finesse of the resonator cavity.

The resonator cavity finesse F at a particular wavelength is related to the round trip loss of the resonator at that wavelength and can be determined from the equation:

$$F = \frac{\pi \sqrt{r_1 r_2 e^{-A/2}}}{1 - r_1 r_2 e^{-A/2}} \quad (4)$$

where ($r_1$ and $r_2$ are the mirror reflection coefficients of a linear cavity, and A is the roundtrip intra-cavity loss of the resonator cavity at a particular wavelength, for example absorption by a spectroscopic sample, and scattering/reflection losses from the elements of the resonator cavity or other round-trip losses).

Stabilisation of the laser frequency may be achieved by locking using standardised techniques such as the Pound-Drever-Hall (PDH) locking method routinely employed in the art. The PDH frequency locking technique is widely used in the gravitational wave detection community for a range of applications, including laser frequency stabilization, interferometer longitudinal and alignment control, as well as gravitational wave signal extraction. PDH locking of the laser is the method of choice for ultra-sensitive interferometry and spectroscopic applications. While it is well-established with free-space bulk-optical resonators and solid-state lasers, it can be readily extended to stabilisation of tunable diode laser sources and guided-wave optical system (e.g. optical fibre and waveguide systems).

In general, the output from a tunable laser source is phase modulated (PM) to generate radio-frequency (RF) sidebands on the carrier frequency of the laser output that are used to generate a PDH error signal proportional to the instantaneous difference between the laser frequency and that of a resonance frequency (i.e. a longitudinal mode) of an external reference resonator cavity. The PDH error signal is obtained by an optical heterodyne detection technique of the sidebands produced by the demodulation. This technique determines whether the carrier frequency needs to be adjusted up or down in order to return the laser to the desired frequency using a high gain negative feedback loop which locks the laser to the mode of the reference cavity. Alternatively, the PDH error signal can be used to adjust the cavity length up or down in order to return the resonator cavity back into resonance with the laser carrier frequency. The reference resonator cavity is typically a high finesse cavity such as a Fabry Perot interferometer with finesse greater than at least 50. The longitudinal mode of the cavity to which the laser is locked is generally chosen to be the closest in frequency to the free-running output of the laser. This choice assists in minimising the amount of tuning that needs to be applied to the laser frequency to bring it into lock with the cavity resonance mode and thus enable the tracking of variations in the cavity resonance without losing the lock [further information on the PDH locking technique may be found in many sources such as Black ED, "An introductions to Pound-Drever-Hall laser frequency stabilization", American Journal of Physics, Vol. 69, No. 1, 2001, the contents of which are wholly incorporated herein by cross-reference]. The laser is typically phase modulated between about 10's to 100's of MHz using a suitable phase modulator as would be appreciated by the skilled addressee, for example an electro-optic modulator such as a Pockels cell modulator or a Kerr effect modulator.

The spectroscopic methods disclosed herein utilise the high finesse resonator cavity for the PDH locking scheme for spectroscopic measurements to provide a system capable of shot-noise-limited detection. The resonator cavity is subjected to a loss mechanism, for example a broadband intracavity loss such as an absorption feature in a substance within the cavity, which affects the impedance matching condition of the resonator cavity. Using an amplitude modulated (AM) input beam, which may or may not be the same beam as the phase modulated laser beam locked to a Fabry-Perot resonance of the cavity, the magnitude of the intracavity loss may be used to generate an AM error signal. This AM error signal may be used to drive a high gain negative feedback loop which locks the resonator cavity to the impedance matched condition via a similar heterodyne detection method to that of the PDH technique above [further details on impedance matching of a resonator cavity may be found for example in Slagmolen, B J J et al "Phase-sensitive reflection technique for characterization of a Fabry-Perot interferometer", Applied Optics, Vol. 39, No. 21, 2000, the contents of which are wholly incorporated herein by cross-reference]. Therefore, the AM error signal provides a direct measurement of the intracavity loss in the high finesse cavity as a result of the loss mechanism.

In the methods disclosed herein, the resonator cavity is provided with at least one variable reflectance element, typically the input coupler or reflector (for example a mirror in the case of a free-space resonator or an optical coupler in the case of a guided-wave e.g. fibre resonator) of the resonator cavity.

The electric field reflectivity of the resonator cavity on resonance (i.e. coinciding with a longitudinal mode of the resonator cavity) is given by the relation for a Fabry-Perot interferometer, and yields a purely real value given by $$\frac{E_{refl}}{E_{inc}} = \frac{r_1 - r_2 e^{-A/2}}{1 - r_1 r_2 e^{-A/2}} \quad (5)$$

where $r_1$ and $r_2$ are the electric field amplitude reflection coefficient of the front and rear Fabry-Perot interferometer mirrors (corresponding to input and output reflectors of a resonator cavity) respectively, and A is the roundtrip intracavity loss. The resulting power reflectivity of a resonator cavity is given by the square of Equation 5 and is plotted in trace A (101) of FIG. 1A as a function of mirror power transmission $T_1 = (1-R_1)$ (where $T_1 = t_1^2$ and $R_1 = r_1^2$) of the input reflector of the resonator cavity, where it is assumed $R_2 = 0.9$, and A~0. The corresponding optical phase of the reflected field is plotted in trace B (103) of FIG. 1A. For values of the input transmission $T_1$ of less than 0.1, the cavity response is said to be "under coupled" and the reflected field is in phase. In the regime where $T_1 > 0.1$, the cavity response is said to be "over coupled" and the reflected field incurs a discrete $\pi$ phase flip as seen in Trace B. The variable input reflector element may be practically realised in one arrangement using for example a two mirror Fabry-Perot interferometer, whereby variation in the distance between the two mirrors varies the effective reflectance of the Fabry-Perot element, although many other means of realising a variable input reflector element are also available as would be appreciated by the skilled addressee. One further such example of implementing a variable input reflector element would be using a variable frustrated total internal reflection element to modify the reflectivity of the input reflector.

For the purpose of modelling the response of the resonator cavity to the variation of the reflectance of the input reflector element, a variable electric field coupling coefficient u, is defined. For an optical field (e.g. a laser beam) incident on the variable input reflector with power $|E_{inc}|^2$, where $E_{inc}$ is the electric field amplitude of the laser beam, the variable electric field coupling coefficient is defined such that the transmitted power through the variable input reflector element is given by: $[(1-u^2) \cdot |E_{inc}|^2]$ and the reflected power is given by: $[u^2 \cdot |E_{inc}|^2]$. The coefficients u and v can be related to Equation 5 by the relations: $r_1 = u$; $r_2 = 1$; and $A = 1-v^2$.

To simulate a broadband intracavity loss in the resonator cavity, a coefficient v is defined with similar properties as the variable electric field coupling coefficient u. The associated single pass loss can then be expressed as $\sqrt{(1-v^2)}$. For example, the loss coefficient $\sqrt{(1-v^2)}$ may be simulated by a second variable reflectance element (eg the output coupler of the resonator cavity) whereby for a field with power $|E|^2$ incident on the second variable reflectance element, the power reflected from the second variable reflector back into the resonator cavity is given by: $[v^2 \cdot |E|^2]$ and the power coupled out of the cavity is given by $[(1-v^2) \cdot |E_{inc}|^2]$. These coupling coefficients, u and v, are illustrated respectively in FIGS. 11A and 11B in relation to the variable couplers A and B of the resonator cavity 430 to enable fibre arrangement example of the apparatus for carrying out the CEAMLAS method disclosed herein. With the exception of the cavity losses as defined by coefficients u and v, the resonator cavity is considered in the following discussion to be lossless.]

The combination of coupling and loss coefficients u and v allows a detailed numeric model of the single pass cavity loss sensitivity of a suitable apparatus or system using the presently described spectroscopic methods to be developed as follows.

For a given input incident laser field $E_{inc}$, when the input field is locked to a resonance of the cavity, e.g. via a PDH locking scheme, the response of the resonator cavity is purely real and, for values of $v^2$ approaching unity, can be expressed in terms of coefficients u and v as $$\frac{E_{out}}{E_{inc}} = \frac{\Delta r}{1 - uv} \quad (6)$$

where $E_{out}$ is the output optical field from the cavity and $\Delta r = (u-v)$ is the coupling ratio difference is between u and v. The optical phase of the output field therefore incurs a discrete $\pi$ phase flip as $\Delta r$ goes through zero. This corresponds to changing the cavity impedance from "undercoupled" ($\Delta r > 0$) to "over-coupled" ($\Delta r < 0$). The special condition where $\Delta r = 0$ is referred to as "impedance-matched".

Practically, radio-frequency (RF) laser modulation interferometry techniques are used to a) lock the laser to resonance; and b) interrogate the impedance coupling condition of the locked cavity. An example means of locking the incident laser radiation to a resonance of the cavity may employ PDH frequency locking by phase modulating (PM) a tunable laser system. After the laser is locked to resonance, the incident radiation is further modulated using an amplitude modulation (AM) scheme to introduce AM sidebands at a frequency, $\omega_{AM}$, such that $\omega_{AM}$ is outside the full-width half-maximum (FWHM) of the particular longitudinal resonance mode of the resonator cavity to which the laser is locked. In other arrangements the frequency of the AM modulation may be reduced such that the AM sidebands are within the FWHM of the longitudinal resonance mode of the resonator cavity, however, it will be appreciated that the performance of the detection of the loss within the cavity in this arrangement may be reduced compared with the case where the AM sidebands fall outside the FWHM of the cavity resonance.

Figure 2:
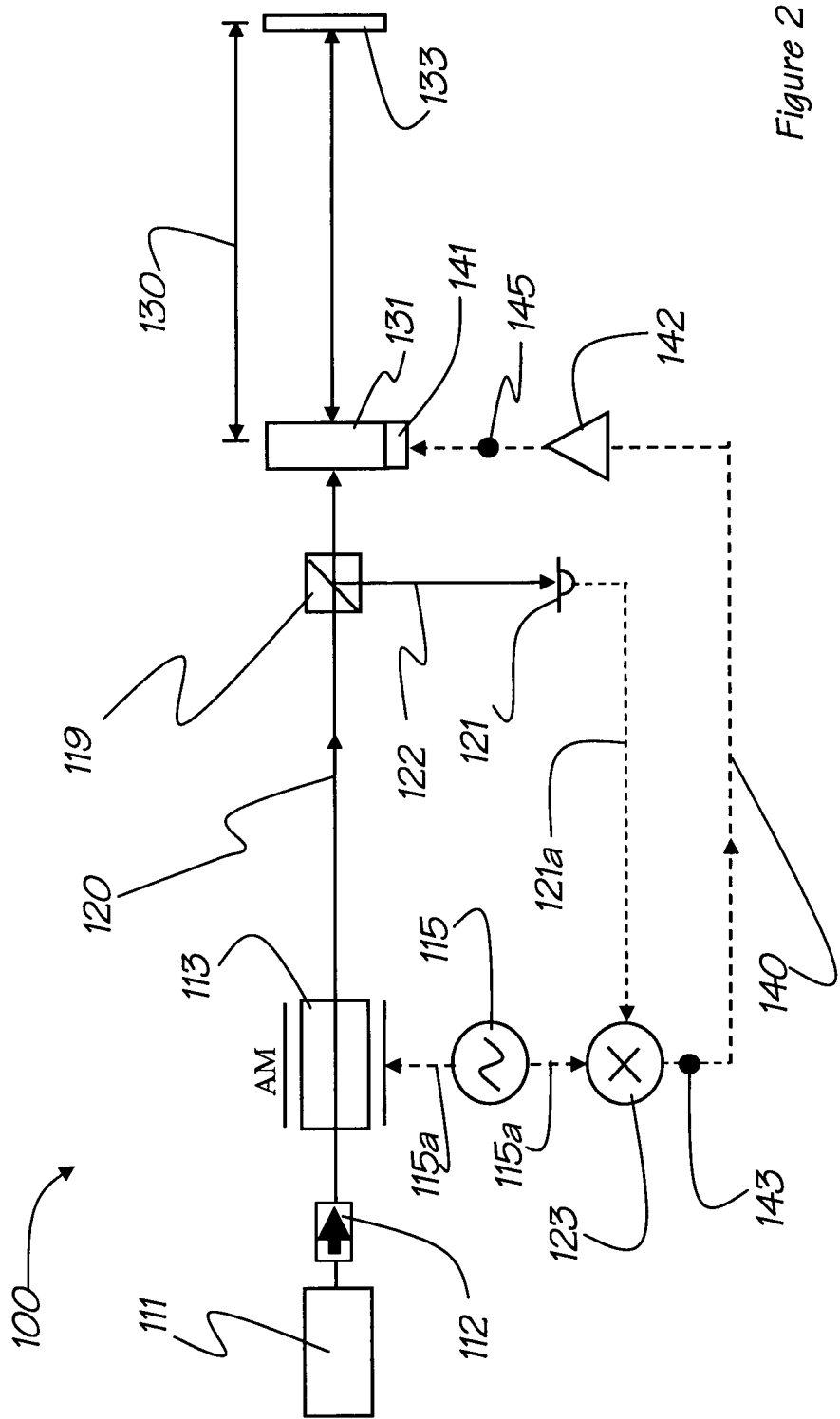
FIG. 2 is a simplified schematic depiction of an arrangement of an apparatus for carrying out the cavity enhanced amplitude modulated laser absorption spectroscopy method.

A schematic depiction of an arrangement of a suitable apparatus for realising the cavity-enhanced-amplitude-modulated-laser-absorption-spectroscopy (CEAMLAS) method is shown in the system 100 depicted in FIG. 2. For the sake of conceptual clarity, depiction of the standard PDH locking loop has been omitted. In the depiction of this and subsequent arrangements, optical paths are depicted as solid lines and electrical interconnections between components are depicted as broken lines. The electrical interconnections may be transmission lines for transmission of an electrical control signal or other detected electrical signal. For clarity of the following descriptions, electrical interconnections are identified solely by the signal (e.g. a modulation signal or error signal) that is present on a particular interconnection. It will be appreciated that the realisation of such interconnections is known in the art for example by use of suitable cabling eg coaxial or other cable.

An amplitude modulated light field 120 is used to interrogate the impedance matching condition of a resonator cavity 130, wherein the resonator cavity 130 comprises input and output reflector elements 131 and 133 respectively. In the arrangements of the system 100 described herein, the input reflector element 131 is a variable reflectivity input reflector element where the reflectivity of reflector element 131 can be adjusted in response to a control signal. The light field 120 is generated by laser 111 having a centre output frequency $\omega_o$ (also referred to herein as the carrier frequency) which is amplitude modulated by a modulator 113 at a frequency $\omega_{AM}$ 115a generated by frequency generator 115. Amplitude modulator may be any type of amplitude modulator as would be appreciated by the skilled addressee, examples of which may include an optical chopper or acousto-optic modulator. The modulation depth provided by amplitude modulator 115 may be in the range of 0.01% to 100% as required.

An optical isolator 112 is also used to prevent back-reflections from the resonator cavity reaching the laser 111 which may cause instabilities in the laser carrier frequency $\omega_o$.

The AM reflected field 122 that emerges from the resonator cavity 130 is directed by a beam-splitter 119 and detected on a high speed photodetector 121. The amplitude modulation imparted on the incident optical field 120 by amplitude modulator 113 generates AM sidebands that are sufficiently offset from the carrier (the laser beam at frequency $\omega_o$) such that they do not effectively interact with the resonant (longitudinal) mode of the cavity to which the laser carrier is locked. The reflected field 122 from the cavity can then be described by the relation:

$$E_{out} = P_{inc}\left[e^{-i\omega_0 t}\frac{\Delta r}{1 - uv} + \frac{\beta}{2}e^{-i(\omega_0 - \omega_m)t} + \frac{\beta}{2}e^{-i(\omega_0 + \omega_m)t}\right] \quad (7)$$

where $P_{inc}$ (is the field amplitude of the incident laser; such that $P_{opt} = |E_{out}|^2$ is the incident laser optical power; $\beta$ is the AM modulation depth, such that $\beta << 1$; $\omega_0$ is the resonant frequency; and it is assumed that the optical power of the sidebands are reflected by the variable input reflector 131 with negligible attenuation. The resonant carrier at frequency $\omega_o$ on the other hand is actively held on resonance with the cavity mode and so interacts with the cavity mode before being coupled to the photodetector 121, where it interferes with the AM sidebands to generate a modulated photocurrent 121a.

The photocurrent 121a from detector 121 is demodulated by demodulator element 123 to extract an output 140 —the AM error signal—which is directly proportional to the real component of the reflectivity from the resonator cavity 130. The voltage output AM error signal 140 can be written as $$V_{sig} \approx \rho\beta P_{opt} R_{pd} \frac{\Delta r}{1 - uv} \quad (8)$$

where $\rho$ is the photodetector responsivity; and $R_{pd}$ is the trans-impedance gain of the photodetector 121. This demodulated output is plotted in trace C (105) of FIG. 1A. It can be seen from plot 105 of FIG. 1A that near resonance (i.e. near the impedance matching point $T_1 = 0.1$) the AM error signal 140 is a linear, zero crossing error signal that determines both the amplitude/magnitude and direction of the displacement from the impedance matching point of the resonator cavity 130. This is in contrast to the reflected optical power of trace A (101) which exhibits a turning point at the impedance matching point of the resonator cavity 130 with no first order response to impedance changes.

Figure 1B:
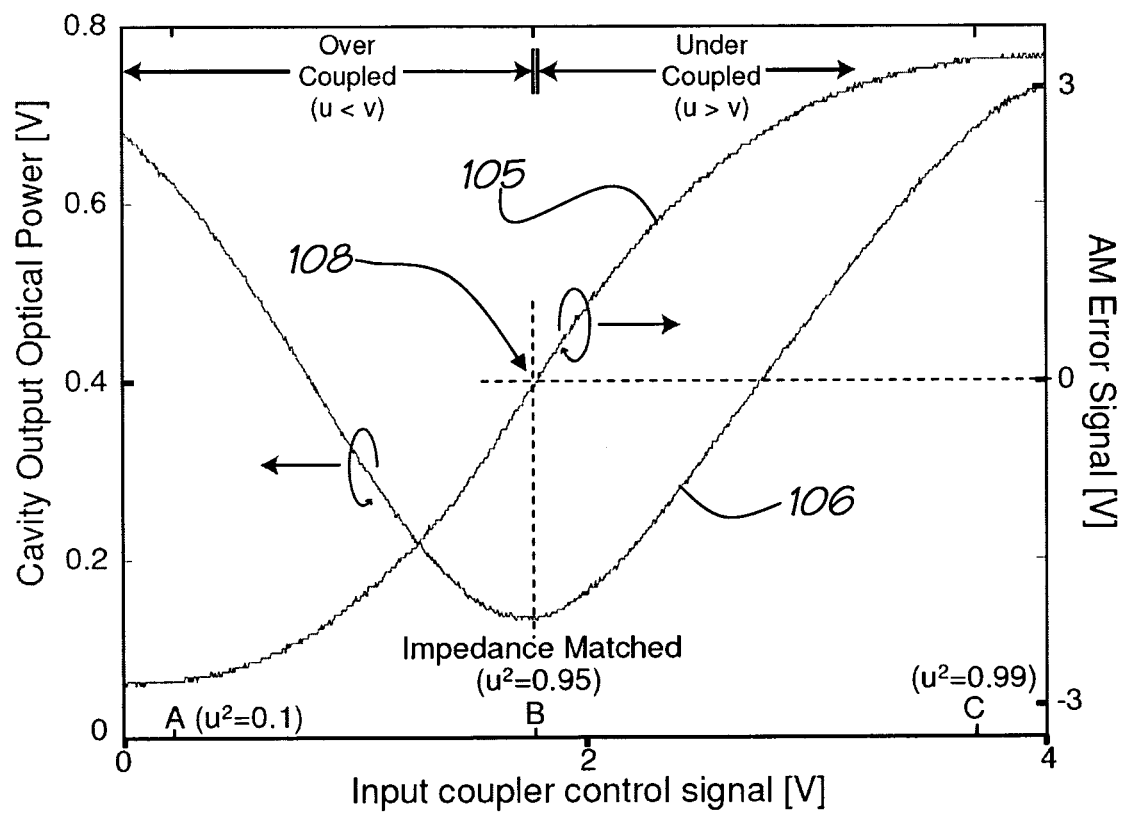
FIG. 1B is an overlaid graph of the reflected cavity output power and the AM error signal expanded to highlight the characteristics of the error signal about a cavity resonance when impedance matched.

To further demonstrate the utility of the AM error signal, FIG. 1B is a graph where the AM error signal 105 is plotted against the reflected optical power 106 from the resonator cavity 130 with the laser 111 locked to a cavity resonance and the reflectance of the variable reflector element 131 scanned through impedance matching. As can be seen the AM error signal crosses zero where the reflected power 101 is minimum (i.e. at point 108 of FIG. 1B). On either side of this optimum point 108, the transmitted power increases as the impedance matching deteriorates. At the extreme edges of FIG. 1B, the AM error signal 105 saturates indicating that the on resonance reflectivity of the carrier is approaching unity for both the over-coupled ($u^2$ approaches zero on the left hand side) and the undercoupled ($u^2$ approaches unity on the right hand side) extreme.

From Equation 8 and plot 105 of FIG. 1B, it can be seen that the demodulated signal is positive for under-coupled cavities and negative for over-coupled cavities. When the cavity is exactly impedance matched, $V_{sig}=0$. Hence, the AM error signal yields a direct measure of the impedance coupling condition of the cavity.

As the impedance matching condition of a cavity directly depends on both the input coupler reflectivity and the cavity loss, the AM error signal determines not only the impedance matching condition of the cavity but also the cavity loss relative to the input coupler.

Thus, it has been found that the AM error signal 140 can be used as a sensitive and direct measure of the single pass loss in the resonator cavity 130. It can be shown that the sensitivity of $V_{sig}$ to single pass cavity loss is equal to the limit set by Equation 2, when the cavity is operated at the impedance-matched point. In addition, when impedance-matched, the AM error signal is zero and the single pass loss measurement becomes a "null" measurement, which advantageously leads to an immunity to low frequency laser intensity noise. It is sufficient that the laser intensity noise be shot noise limited at the frequency of the amplitude modulation $\omega_{AM}$ only. In practice, the amplitude modulation frequency $\omega_{AM}$ can be selected sufficiently high to ensure that this is achieved and active stabilisation of the intensity of the output at the carrier frequency $\omega_o$ from laser 111 is not required.

Additionally, FIG. 1B demonstrates a significant advantage of the present RF cavity interrogation method in that, whilst measuring the reflected optical power yields no first order signal at the impedance matched point, the AM error signal reaches it's maximum slope at this point and yields a large, high sensitivity read out of both cavity impedance and cavity loss.

Figure 3:
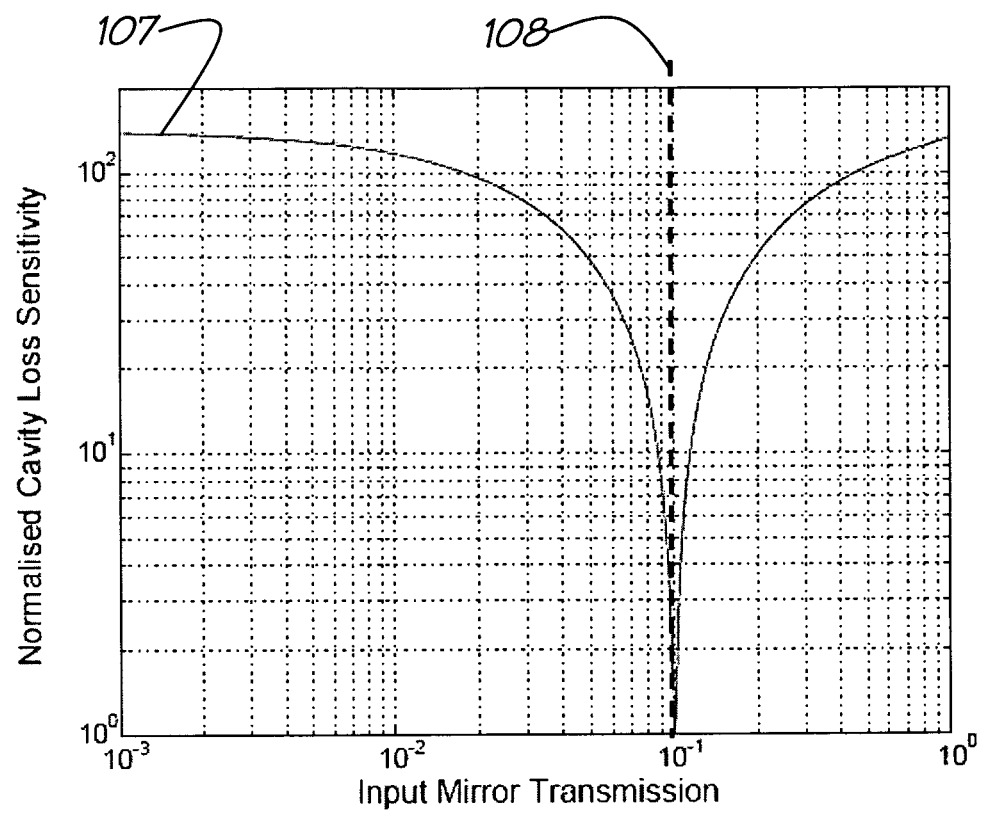
FIG. 3 is a graph of the normalised single pass loss sensitivity as a function of input coupler transmission assuming an amplitude modulation depth assumed here is $\beta=0.01$ such that the impedance matching condition occurs at an input reflector transmission of 10% (reflectivity 90%)

Using the model developed above, FIG. 3 shows a graph of the sensitivity 107 of the measurement of the loss of resonator cavity 130, normalised to the impedance matched result, as a function of the transmission $T_1$ of input coupler 131 (where $T_1=10^0=1$ is equivalent to 100% to transmission). The impedance matching condition in this example occurs at an input transmission of $T_1=0.10$ (10%). The amplitude modulation depth ($\beta$) assumed here is $\beta=0.01$ or 1%.

As can be seen, there is a dramatic deterioration in loss sensitivity away from the impedance matching point 108. With only modest changes in input coupler transmission, the sensitivity to losses in resonator cavity 130 deteriorates by more than a factor of one hundred.

Hence for optimum intra-cavity loss sensitivity, the resonator cavity 130 should be kept at the impedance-matched condition. This is implemented by using $V_{sig}$—the AM error signal 140—to actuate the variable input reflector 131 in an active negative feedback loop, to force the resonator cavity 130 to operate at the impedance matching point 108 at all times and thus preserve the optimum sensitivity of this technique. The impedance matching control actuator element 141 of FIG. 2 performs this task by acting on the variable reflector element 131 to adjust the reflectivity of the input reflector 131 to bring the cavity back into the impedance matched condition. This may be implemented by using a device such as a servo drive element for adjusting the characteristics of the variable input coupler 131 thereby to vary the reflectivity of the reflector 131 as required. An example of such a drive element is a piezoelectric transducer (PZT) although other suitable actuator devices are available as would be appreciated by the skilled addressee for the particular arrangement in use. A servo amplifier 142 is typically used to amplify the error signal 140 into a suitable range for driving the actuator 141.

In addition to optimising the cavity loss sensitivity, actuating the input coupler 131 also improves the dynamic range of this technique. With closed loop operation, the system can track large loss changes within the cavity 130 whilst maintaining the cavity at the impedance matched condition. Under these conditions, the system is limited only by the dynamic range of the actuator 141 and the variable input coupler 131 and not the linear region of the AM error signal 140. In practice, actuators with a dynamic range of zero to one hundred percent are readily available ensuring that a single cavity system can accommodate a wide range of cavity loss measurements.

It is noteworthy, however, that with a large increase in loss, the cavity finesse F in Equation 2 decreases, thereby increasing the shot noise limit, which thus degrades the overall sensitivity of the system.

Closed loop measurements of the cavity loss can be made at the "actuator point" 145 in FIG. 2 for signals at frequencies where the gain of the actuator 141 is large; the low frequency range extending down to DC. For fast cavity loss processes above the unity gain bandwidth of the impedance matching actuator 141, the "error point" 143 of FIG. 2 provides an effective "open loop" error signal readout. The error signal (either in open loop or closed loop configuration) may then be used to determine a parameter either located in or which affect the loss in the resonator (e.g. by affecting the reflectivity of a resonator reflector) and/or a change in such a parameter. In this way the systems described herein are capable of either detecting and/or monitoring a parameter which is coupled to the resonator in such a manner that it affects the loss in the resonator cavity. This determination of the parameter or change in a parameter from the error signal may be assisted by the use of a calculator, computer or some other means such as a dedicated electronic circuit with a readout. The determination may also be assisted by the use of digital-to analogue or analogue-to-digital converters which may be coupled to the demodulator or other suitable component as depicted in the arrangements described herein.

Figure 4A:
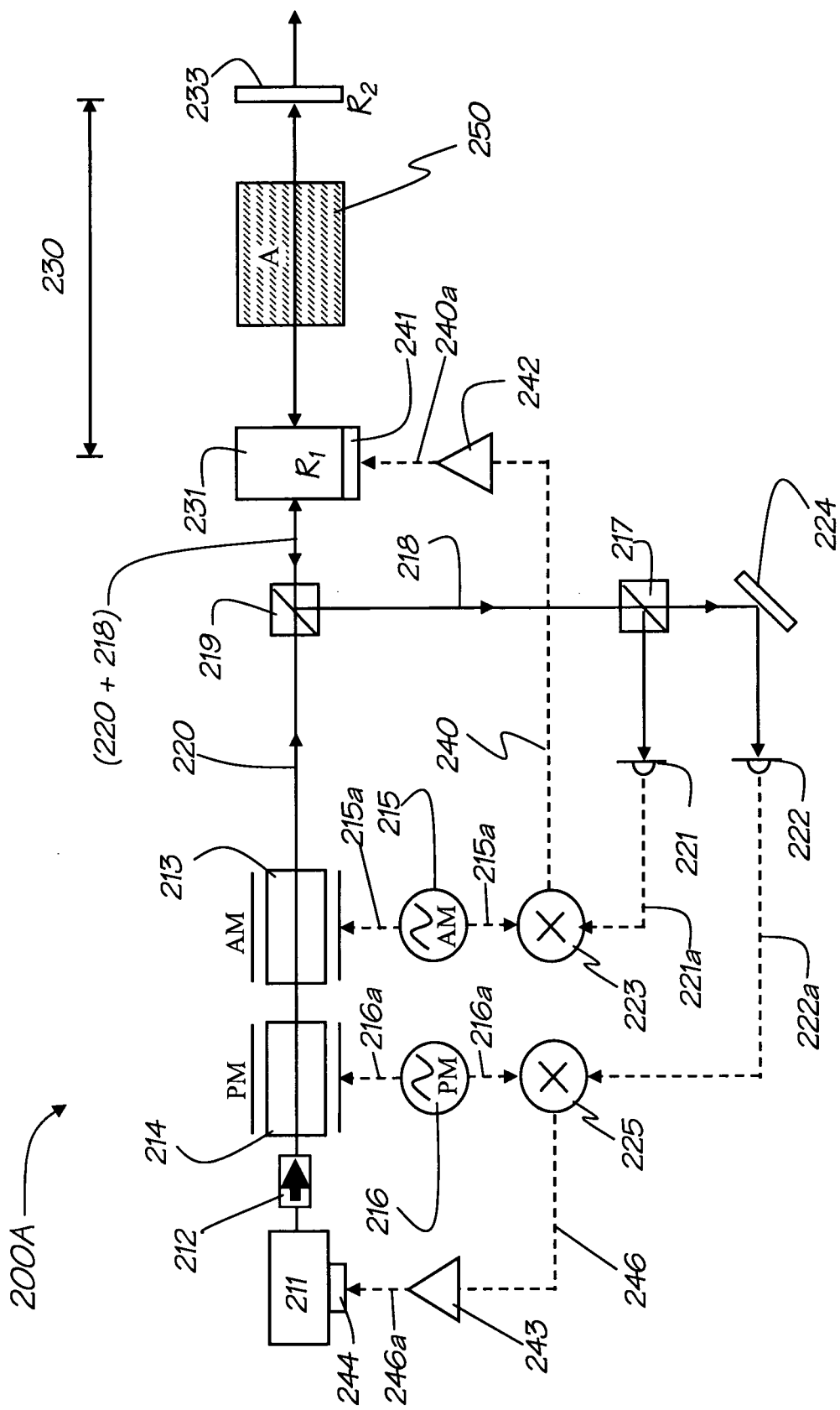
FIGS. 4A and 4B are a schematic depictions of a free space arrangement of an apparatus for carrying out the cavity enhanced amplitude modulated laser absorption spectroscopy method showing both the phase-modulated frequency locking control loop for locking the laser to a cavity resonance and the amplitude modulated impedance matching control loop for monitoring the loss within the resonator cavity; where

A first arrangement 200A of an exemplary apparatus for performing the cavity enhanced spectroscopy method is depicted schematically in FIG. 4A as a free space arrangement which may be used for example for detection of an absorbing gaseous species within a resonator cavity. The output from a tunable laser 211 is passed through a suitable optical isolator 212 and is both phase modulated and amplitude modulated by PM and AM modulators 214 and 213 respectively. The optical isolator 212 prevents back-reflections from affecting the laser. The modulated beam 220 is incident on a resonator cavity 230 comprising a variable input reflector element $R_1$ (231) and an output reflector $R_2$ (233). A loss mechanism 250 is present in the resonator cavity 230.

The light 218 reflected from the resonator cavity 230 is directed by beamsplitters 219 and 217 and turning mirror 224 to photodetectors 221 and 222 which respectively produce modulated photocurrents 221a and 222a.

Phase modulator 214 is modulated by a first function generator 216 at a frequency $\omega_{PM}$ (216a generated by signal generator 216), and is used for a frequency locking control loop to keep the laser optical frequency resonant with a longitudinal mode of the resonator cavity 230 formed by $R_1$ and R$_2$. This is performed by, using demodulator 225, demodulating the detected signal 222a from photodetector 222 with the output of function generator 216 to generate a PM error signal 246 which is fed back to the tunable laser 211 via a laser frequency actuator 244 (via amplifier 243 to produce an amplified PM error signal 246a) which varies the laser frequency in response to the PM error signal 246.

Similarly, amplitude modulator 213 is modulated by a second function generator 215 at a frequency $\omega_{AM}$ (215a generated by signal generator 215), and is used to implement the impedance matching to monitor the loss in the resonator cavity 230 caused by the loss mechanism 250, which may be for example an absorbing gaseous or liquid species. This is performed by, using demodulator 223, demodulating the signal detected 221a from photodetector 221 with the output of function generator 215 to generate an AM error signal 240 which is fed back to the variable input reflector 231 via a reflector actuator 241 (via amplifier 242 to produce an amplified AM error signal 240a) which varies the reflectivity of reflector R$_1$ in response to the AM error signal as described numerically above. Alternatively (not shown), the output reflector R$_2$ may be a variable reflector and the actuator may act on to the output reflector R$_2$ to maintain the cavity in the impedance matched condition.

Figure 4B:
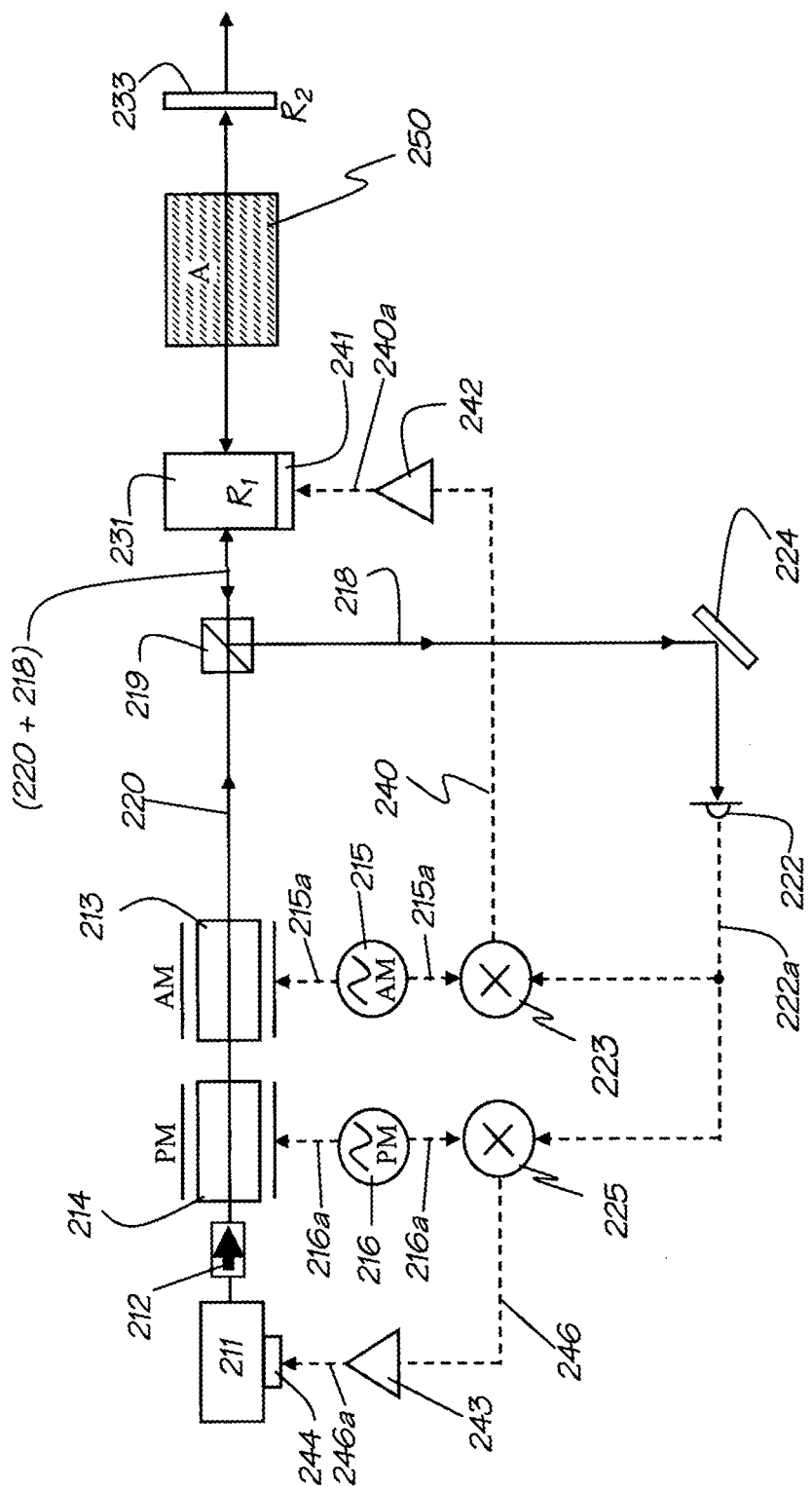

FIG. 4B shows a alternate arrangement 200B of the system of FIG. 4A using a single photodetector detector 222, the output of which is directed to both demodulators 223 and 225 and demodulated to obtain both the AM error signal 240 and the PM error signal 246 for both the phase-modulated frequency locking control loop and the amplitude modulated impedance matching control loop respectively.

Figure 4C:
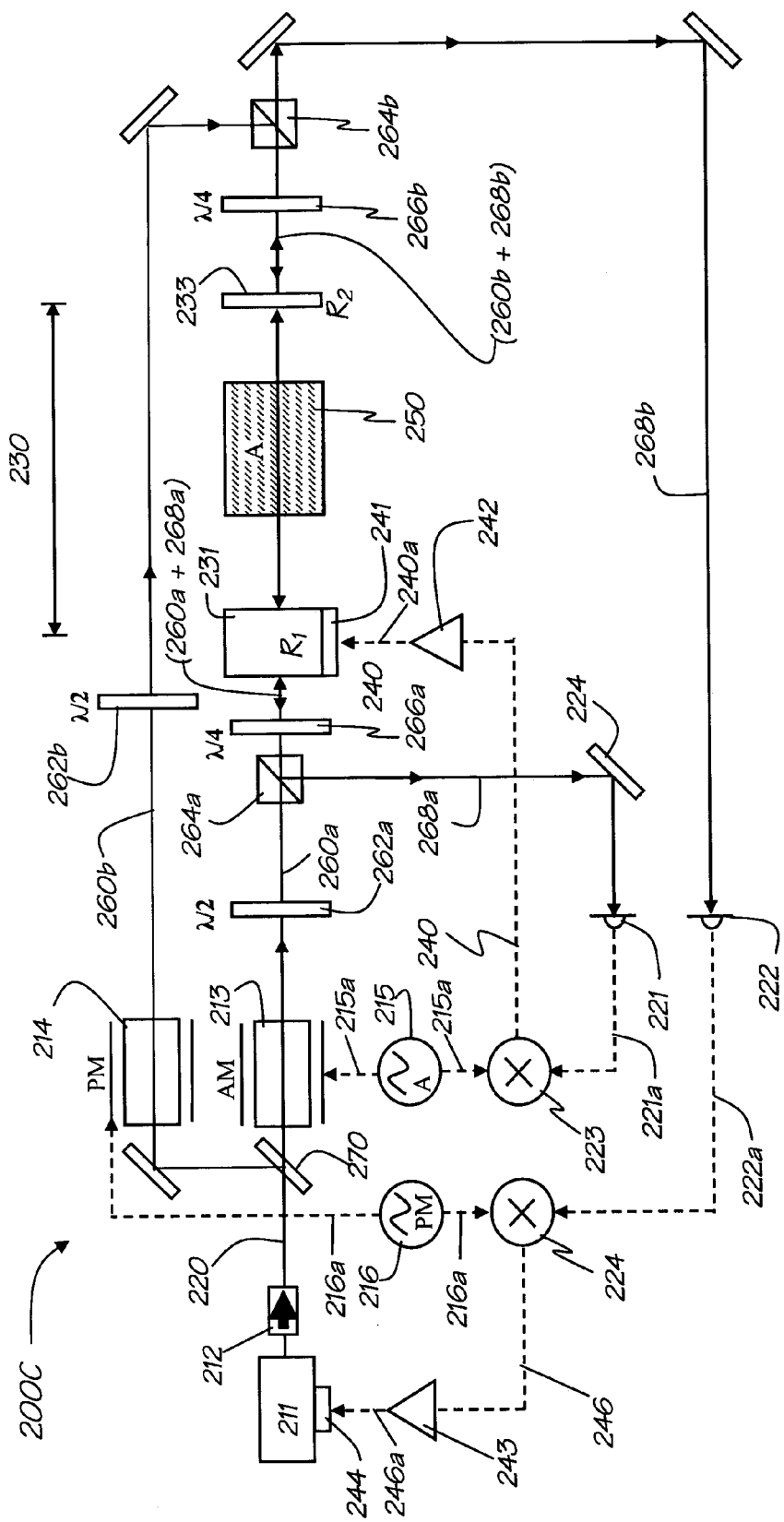
FIG. 4C is an alternate arrangement of the free-space apparatus of FIG. 4A where the phase modulation and the amplitude modulation of the laser beam are performed in parallel.

FIGS. 4A and 4B show arrangements of the CEAMLAS apparatus where the amplitude and phase modulation for each of the control loops is applied to the laser beam from the laser source 211 in series. FIG. 4C on the other hand depicts an alternate arrangement where the amplitude and phase modulation may be applied in parallel.

In FIG. 4C, the beam 220 from laser source 211 is split by a beamsplitter 270 into two portions, the first portion being modulated by the amplitude modulator 213 to form amplitude modulated beam 260a and the second portion being phase modulated by modulator 214 to form phase modulated beam 260b. AM modulated beam 260a is directed to the resonator cavity 230 as before through the variable input reflector element R$_1$ 231. The PM modulated beam 260b is directed into the cavity via an alternative reflector, for example through the output reflector 233. In this arrangement, the PM and the AM modulations must be selected such that they are orthogonal in polarisation to minimise cross-talk between the two separate modulations. This is achieved by the insertion into beams 260a and 260b of suitable polarisers arranged such that the beams are orthogonally polarised. Suitable polarisers are known in the art. Polarisation rotation elements may also be employed as required in the beams to achieve the desired polarisation direction, for example half-wave plates 262a and 262b of FIG. 4C. Polarising beamsplitters 264a and 264b and quarter-wave plates 266a and 266b may also be used to further manipulate the polarisation of the modulated beams 260a and 260b. This enables the polarisation of the reflected beams 268a and 268b (from reflectors 231 and 233 respectively) to be chosen so that only the reflected beams are directed by polarising beams splitters 264a and 264b respectively to detectors 221 and 222. Reflected beams 268a and 268b are then each demodulated as above to obtain the AM and PM error signals respectively. It will be recognised that the addition of such polarisation control measures are advantageous as they prevent crosstalk between the AM and PM modulated light beams being incident on the detectors 221 or 222 which would degrade the detected, signal to noise ratio. For example, in the absence of any additional polarisation control measures, any AM modulated light which may leak from the cavity 230 through output reflector 233 would be incident on detector 222 which would degrade the PM signal detection performance. This is prevented in the present arrangement since any AM modulated light transmitted through reflector 233 has its polarisation (after passing through quarter-wave plate 266b) orthogonal to the PM modulated light 268b reflected from reflector 233, and therefore is reflected by polarising beamsplitter 264b whereas the reflected PM modulated light 268b is transmitted through beamsplitter 264b to be detected by detector 222. Similarly, any PM modulated light which leaks from the input reflector 231 is prevented from being directed to detector 221 and degrading the AM detected signal. The polarisation of any leakage PM modulated light transmitted from the cavity 230 through reflector 231 (after passing through quarter-wave plate 266a) is orthogonal to the AM modulated light 268a reflected from input reflector 231 and is thus transmitted through polarising beamsplitter 264a whereas the reflected AM modulated light 268a is reflected by beamsplitter 264a to be detected by detector 221.

Also in this arrangement, a shift in the carrier frequency of one or other of the beams 260a or 260b may be applied, for example using an acousto-optic modulator to impart an offset of say a few GHz, however, care must be taken such that the resonator cavity 230 is doubly resonant at the carrier frequency of both beams 260a or 260b. In particular, the phase modulated beam 260b must be co-resonant with the amplitude modulated beam 260a within the resonator cavity 230 such that it assists in maintaining the amplitude modulated beam 260a at or near resonance with the cavity. In this arrangement, other methods of separating the AM and PM modulated beams and preventing cross-talk may by employed such as by the use of spectral filters or dichroic reflectors to selectively produce error signals for impedance matching and/or loss measurement, and frequency locking.

In one example arrangement, the laser source 211 may be a frequency shifted laser source comprising a fundamental frequency, a potion of which is frequency shifted to a harmonic frequency of the fundamental frequency (for example a portion of a Nd:YAG laser beam with fundamental frequency of 1064 nm may be frequency doubled to give a harmonic beam at 532 nm), such that the output of the laser comprises a beam at the harmonic frequency and a beam of residual light at the fundamental frequency. The beamsplitter 270 may then be a dichroic mirror adapted to direct, for example the beam at fundamental to the phase modulator 214 while the beam at the harmonic frequency is amplitude modulated by modulator 213 (if desired, the dichroic may be adapted for the reverse situation such that the beam at the fundamental frequency is amplitude modulated). Having the phase and amplitude modulated beams being harmonics or multiples of each other may be advantageous in the selection of reflectors (i.e. 231 and 233) for the resonator cavity 230 with appropriate characteristics such that both the amplitude and the phase modulated beams 260a and 260b are resonant within the cavity.

Figure 4D:
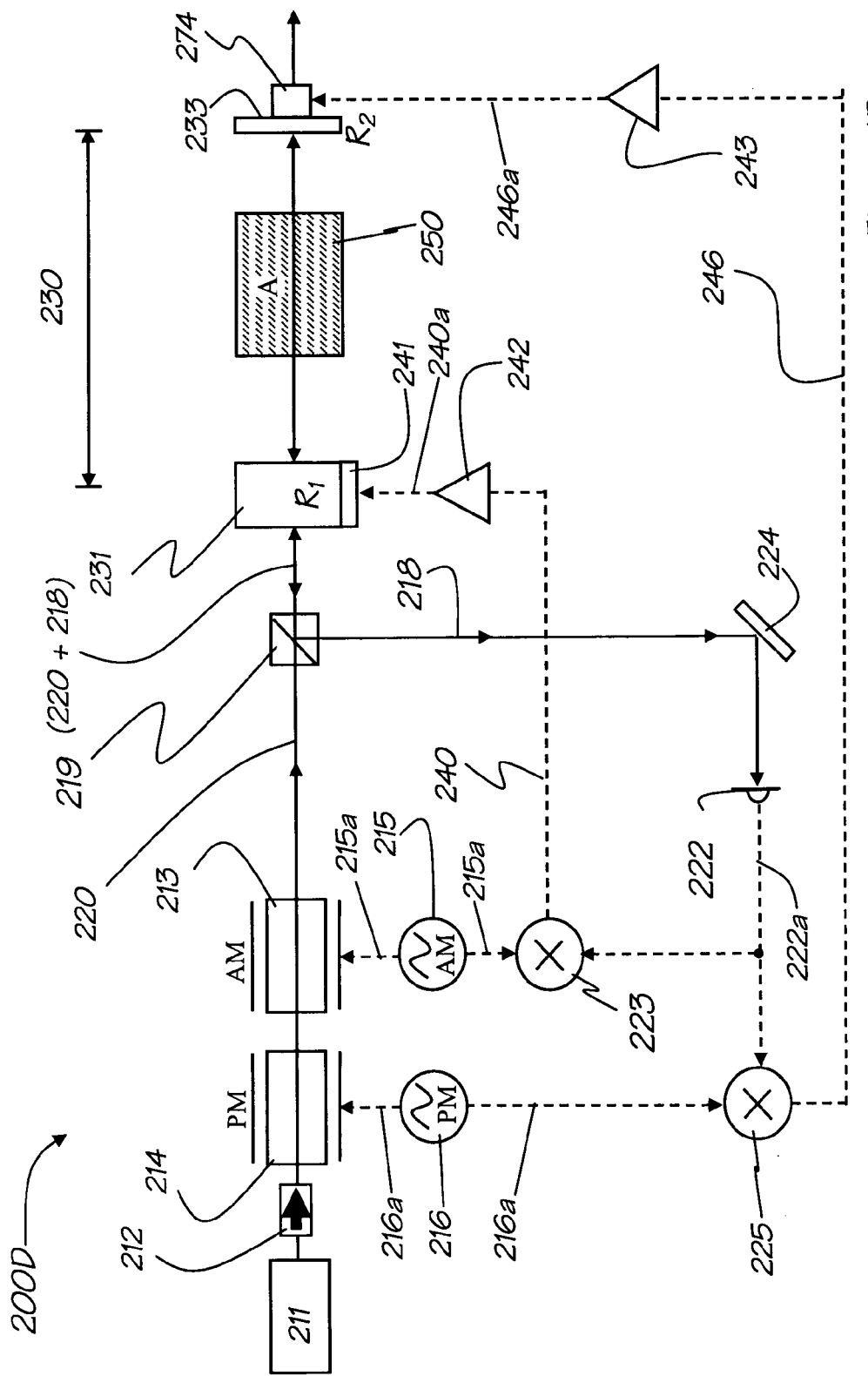
FIG. 4D is an alternate arrangement of the arrangement of FIG. 4B.

FIG. 4D depicts a further arrangement similar to that of FIG. 4B wherein the resonance characteristics of the resonator cavity 230 are modulated in response to the PM error signal 246 rather than the laser frequency itself as per the previous arrangements, to maintain the cavity frequency locked to the laser carrier frequency (in this arrangement, the carrier frequency can be treated as being fixed). To achieve this, an additional actuator 274 is provided on the output reflector 233 which actuated in response to the PM error signal 246. Actuator 274 acts to either increase or decrease the cavity length in response to the PM error signal thereby to modify the cavity resonances to bring the cavity back into lock due to changes in the cavity loss. It will be appreciated that when the cavity loss changes and actuator 241 adjusts the cavity length to maintain the impedance matched condition, this necessarily also introduces an additional phase shift in the cavity resonances. The arrangement in FIG. 4D may be advantageous in particular circumstances, as it may provide a more direct method of maintaining the lock between the carrier frequency and the cavity resonance due to the decoupling from the actuation of the cavity to maintain the impedance matched condition.

In alternate arrangements still, it is envisaged that a suitable scheme may be used where the amplitude and phase modulators are placed in parallel using two separate laser sources and, the output from the first laser source being phase modulated to generate a PM modulated beam for locking to the cavity and the output from the second laser source being amplitude modulated to generate an AM modulated beam for measurement of the cavity losses. Again, the reflectors and of the resonator cavity must be selected such that the resonator is doubly resonant for the carrier frequency of both AM and PM modulated beams. A coupling element may also be provided between the two lasers such that the relative carrier frequencies of the two laser sources may be monitored and or controlled.

Figure 5:
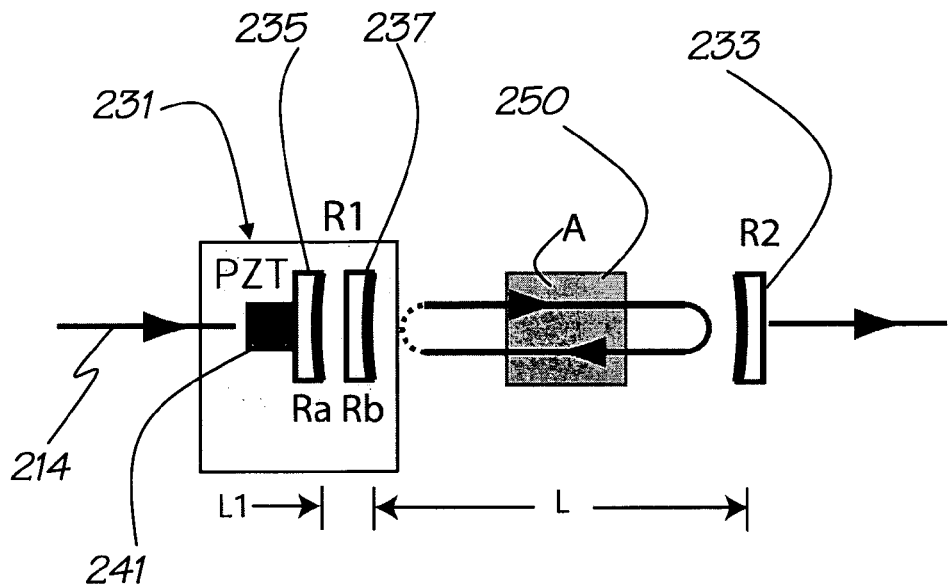
FIG. 5 is a schematic depiction of an arrangement of a variable reflectivity element for use in the free-space apparatus for cavity enhanced amplitude modulated laser absorption spectroscopy.

In the present arrangements of the free-space CEAMLAS apparatus 200A to 200D, the variable reflector element $R_1$ (231) may be implemented by a compound reflector element comprising more than one reflectors. An example of such is a variable reflector 231 is a two-mirror Fabry-Perot element as depicted in FIG. 5. In this arrangement, the variable reflector element 231 comprises reflectors $R_a$ and $R_b$ (235 and 237 respectively). The reflectivity of reflectors 235 and 237 are each chosen to be in the range of about 50% to 99%. Assuming negligible losses, the combined reflectivity of the reflectors 235 and 237, and thus the total electric field amplitude reflectivity of reflector 231 is given by the relation $$\frac{E_{R_1}}{E_{inc}} = \frac{r_a - r_b e^{i\phi_{ab}}}{1 - r_a r_b} \tag{9}$$

where $r_a$ and $r_b$ are the electric field amplitude reflection coefficients of reflectors $R_a$ and $R_b$ (235 and 237) respectively. An example configuration of an exemplary free-space CEAMLAS apparatus 300 similar to that of FIG. 4A using the variable reflector element $R_1$ (231) of FIG. 5 is depicted schematically in FIG. 5B, wherein like reference numerals refer to like components. The configuration 300 differs from that of configuration 200B of FIG. 4A in a reversal of the positions of the AM and PM demodulators 223 and 225 respectively, such that the detector 221 associated with PM demodulator 225 receives reflected light from beam splitter 217.

The optical phase change $\phi_{ab}$ experienced by the incident optical field as it propagates between reflectors $R_a$ and $R_b$ which is given by the relation:

$$\phi_{ab} = \frac{4\pi n L_1}{\lambda_o} \tag{10}$$

where $L_1$ is the distance between reflectors $R_a$ and $R_b$ and $\lambda_o$ is the wavelength of the incident laser radiation from laser 211 at frequency $\omega_o$. As can be seen from Equations 9 and 10, the reflectivity of the variable reflector element R1 (231) is dependent on the separation between the component reflectors $R_a$ and $R_b$. Thus, the impedance matching condition of the resonator cavity 230 can be maintained by feeding back the AM error signal 240 via amplifier 242 to a piezoelectric transducer (PZT) 241 attached to one of reflectors $R_a$ and $R_b$ which acts to vary the separation distance between the reflectors 235 and 237 which thereby changes the effective reflectivity of $R_1$.

Figure 6:
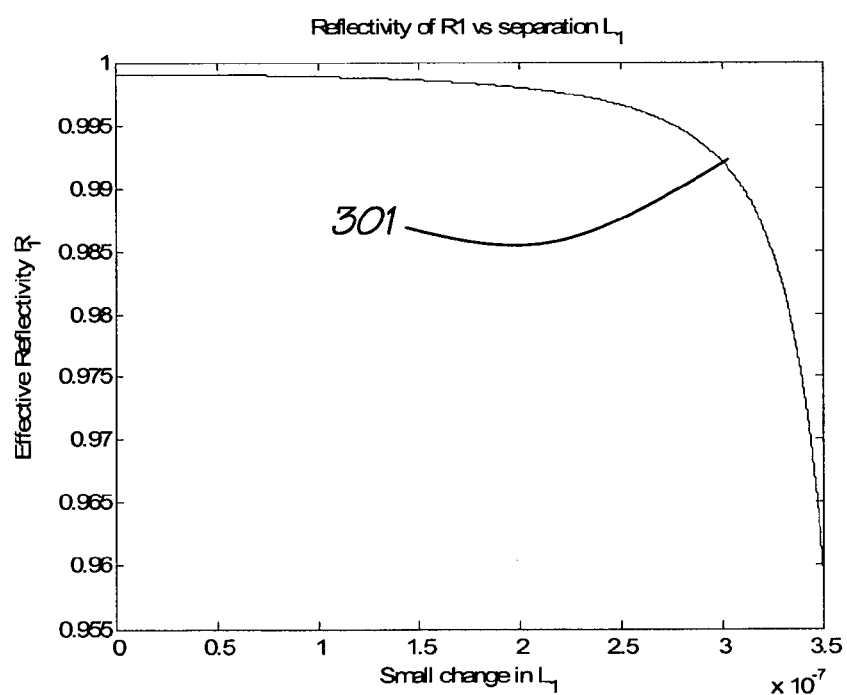
FIG. 6 is a graph of the change in effective reflectivity $R_1$ of the variable reflectivity element of FIG. 5 due to variation in the mirror separation between component reflectors $R_a$ and $R_b$.
Figure 5A:
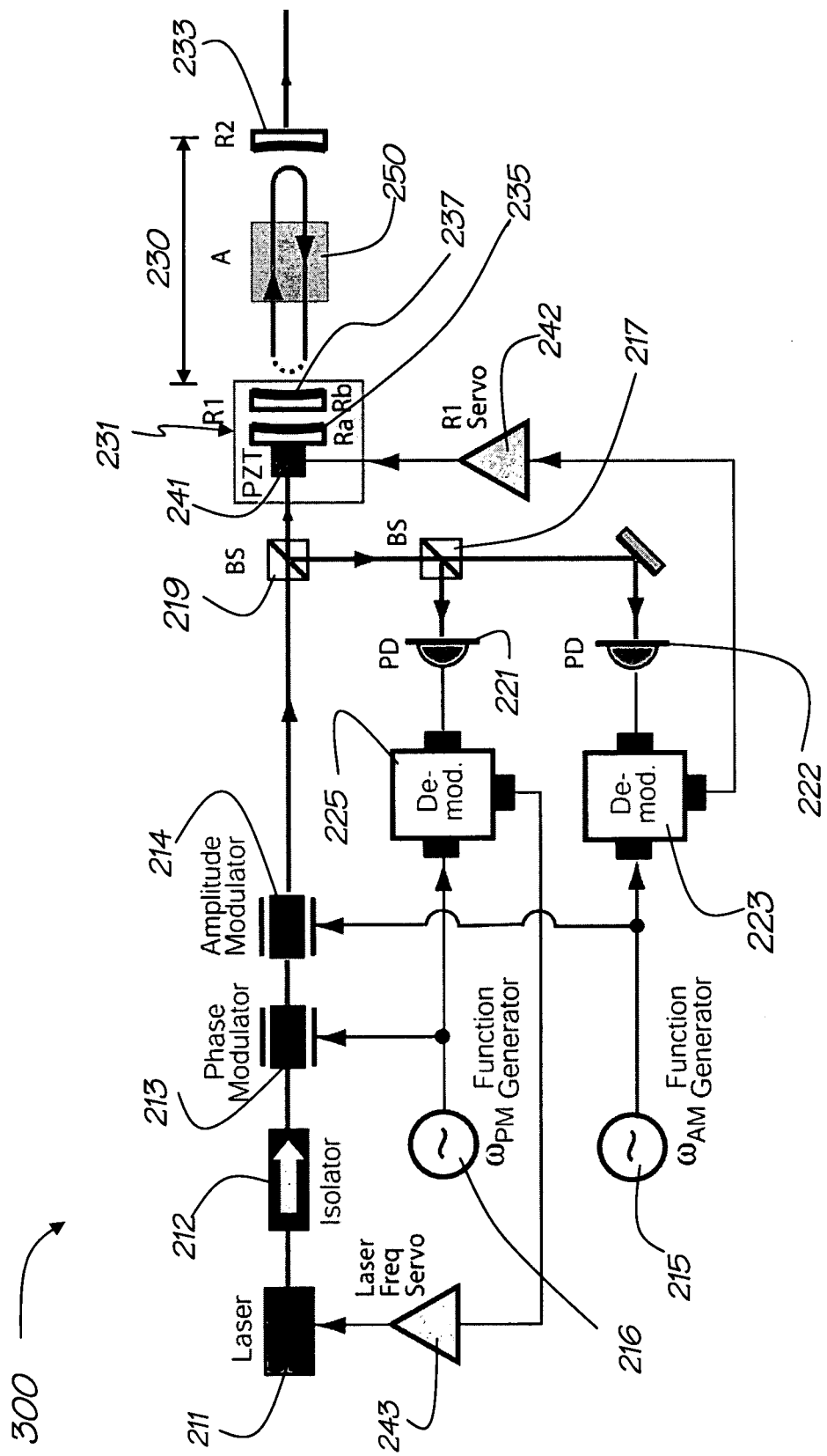
FIG. 5A is a schematic depiction of an alternate configuration of the arrangement of FIG. 4A including the variable reflectivity element of FIG. 5.

This can be seen numerically in FIG. 6 which is a graph 301 of the change in effective reflectivity $R_1$ with a small change in mirror separation $L_1$ between $R_a$ and $R_b$. For this graph, $L_1$ is assumed to be about ~1 mm, and $R_a=R_b=0.94$. The initial condition is anti-resonant, and thus the reflection is a maximum. In general, for a change in the separation of reflectors $R_a$ and $R_b$ over a quarter wavelength of the laser carrier, $R_1$ can be adjusted from a maximum of near unity to a minimum of zero. Hence the mirror pair $R_a$ and $R_b$ behaves as a variable reflectivity mirror, adjustable, for example, via a piezoelectric transducer (PZT).

Thus, in the apparatus of 200 the resonator cavity 230 comprises three mirrors which are assumed to be lossless for the present treatment other than a single-pass absorption loss A within the resonator cavity 230 due to loss mechanism 250.

Figure 7:
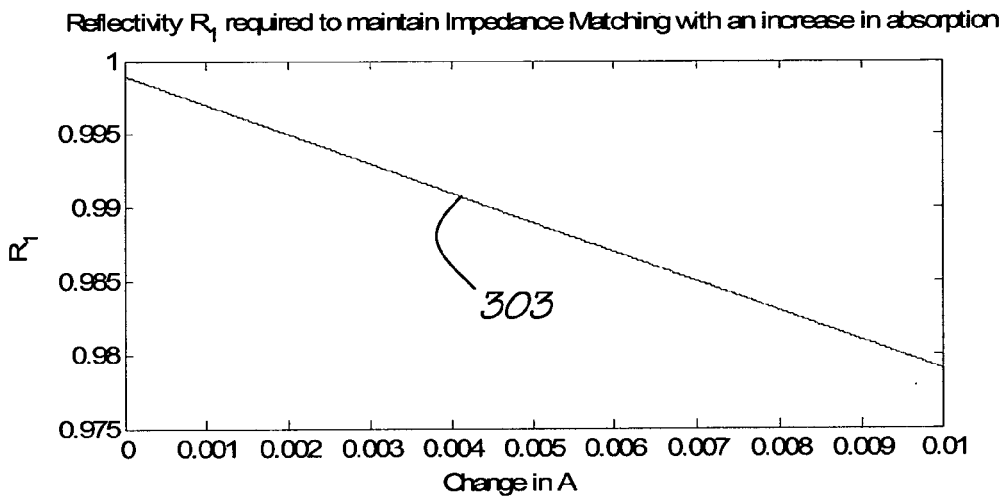
FIG. 7 is a graph of the reflectivity $R_1$ of the variable reflectivity element of FIG. 5 required to maintain the resonator in an impedance matched state as a function of the intra-cavity absorption of the resonator cavity.
Figure 8:
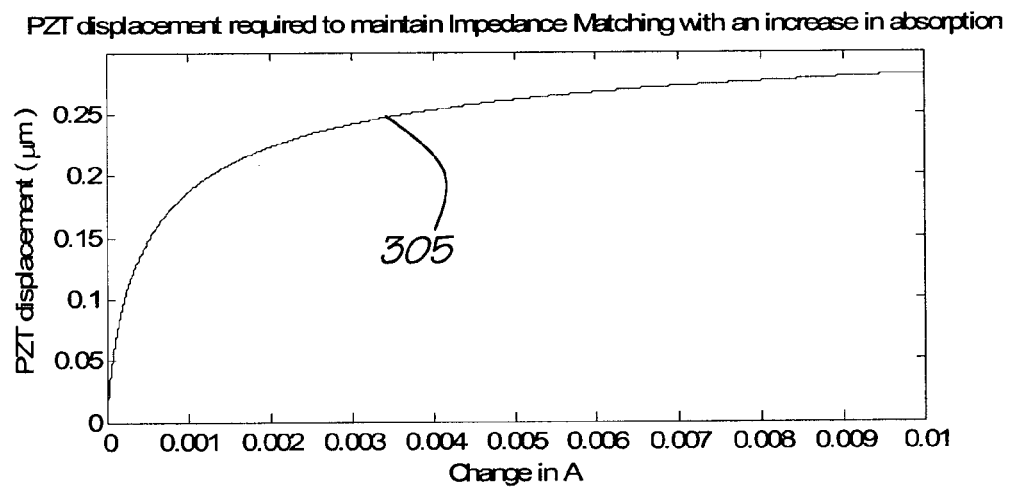
FIG. 8 is a graph of the change in the separation between component reflectors $R_a$ and $R_b$ of the variable reflectivity element of FIG. 5 to maintain the resonator in an impedance matched state as a function of the intra-cavity absorption of the resonator cavity.

Considering the dynamics of the compound resonator cavity 230, where $R_2=0.999$, and the distance L, between $R_1$ and $R_2$, is 0.1 m, an initial round-trip loss A=0, and the cavity is impedance matched, such that $R_1=R_2(1-A)$. Further, assume that the laser is resonant with the cavity (i.e. locked via the PM error signal to a longitudinal resonance of the cavity 230). As the intra-cavity absorption A is increased, $R_1$ needs to be decreased to maintain the impedance-matched condition. The reflectivity $R_1$ required to maintain the impedance matched condition of cavity 230 with respect to the magnitude of the intra-cavity absorption A is shown in the graph 303 of FIG. 7. $R_1$ is varied by actuating on the PZT in the variable reflectivity mirror, which changes the separation $L_1$ between reflectors 235 and 237 and the required displacement to maintain the impedance matched condition of cavity 230 with respect to the magnitude of the intra-cavity absorption A is shown in the graph 305 of FIG. 8. The feedback voltage for actuating the PZT 241 is provided by the AM error signal 240 via amplifier 242 using an amplitude modulation control loop as described above.

Figure 9:
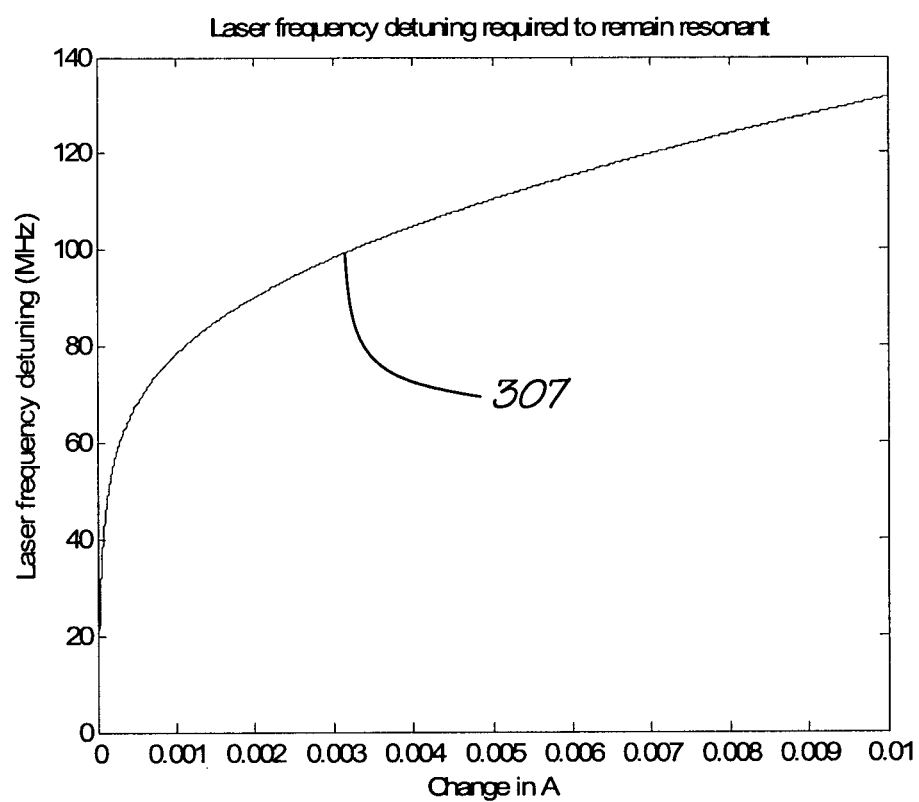
FIG. 9 is a graph of the change in carrier (output) frequency of the laser source required to keep the laser resonant with a cavity resonance (i.e. the laser detuning), as a function of the intra-cavity absorption of the resonator cavity.

It will be appreciated that the variable reflector element $R_1$ (231) has both amplitude and phase response. Therefore, by changing the separation $L_1$ between reflectors 235 and 237, both the amplitude and phase of the effective reflectivity of the variable reflector element $R_1$ (231) is changed. The amplitude response varies the effective reflectivity of $R_1$, whereas the phase response, on the other hand, will detune the resonance of the overall compound cavity. To keep the laser 211 on resonance with the cavity 230, therefore, its frequency must be tuned to track the resultant cavity phase change. The feedback voltage for actuating the frequency of the laser source 211 using a suitable actuator 244 (e.g. a piezoelectric transducer) is provided by the PM error signal 246 via servo amplifier 243 using a PDH control loop as described above. This control loop has the additional advantage of eliminating any mechanical and thermal drifts in the resonator cavity 230. FIG. 9 is a graph 307 the required change in the laser frequency $\omega_o$ of laser 211 in order to keep the carrier frequency resonant with a longitudinal mode of the resonator cavity 230 when there is an increase in intra-cavity absorption.

In general, the effective reflectivity of the variable reflector element $R_1$ (231) is coupled with any tuning of the laser frequency. This in turn tends to move the system away from the impedance-matched condition. The AM control loop, however, would automatically correct for this reflectivity change by feeding back the necessary displacement with the PZT in $R_1$ to restore impedance matching. Hence the process is iterative between the PM and AM control loops to find the optimum $L_1$ and laser frequency solution. One of the ways to minimise the coupling between the two control loops is to keep $L_1$ short. When the ratio $L:L_1$ is large (where L is the separation between reflector elements 231 and 233 as shown in FIG. 5), the coupling between the PM and the AM control loops becomes negligible.

Figure 10:
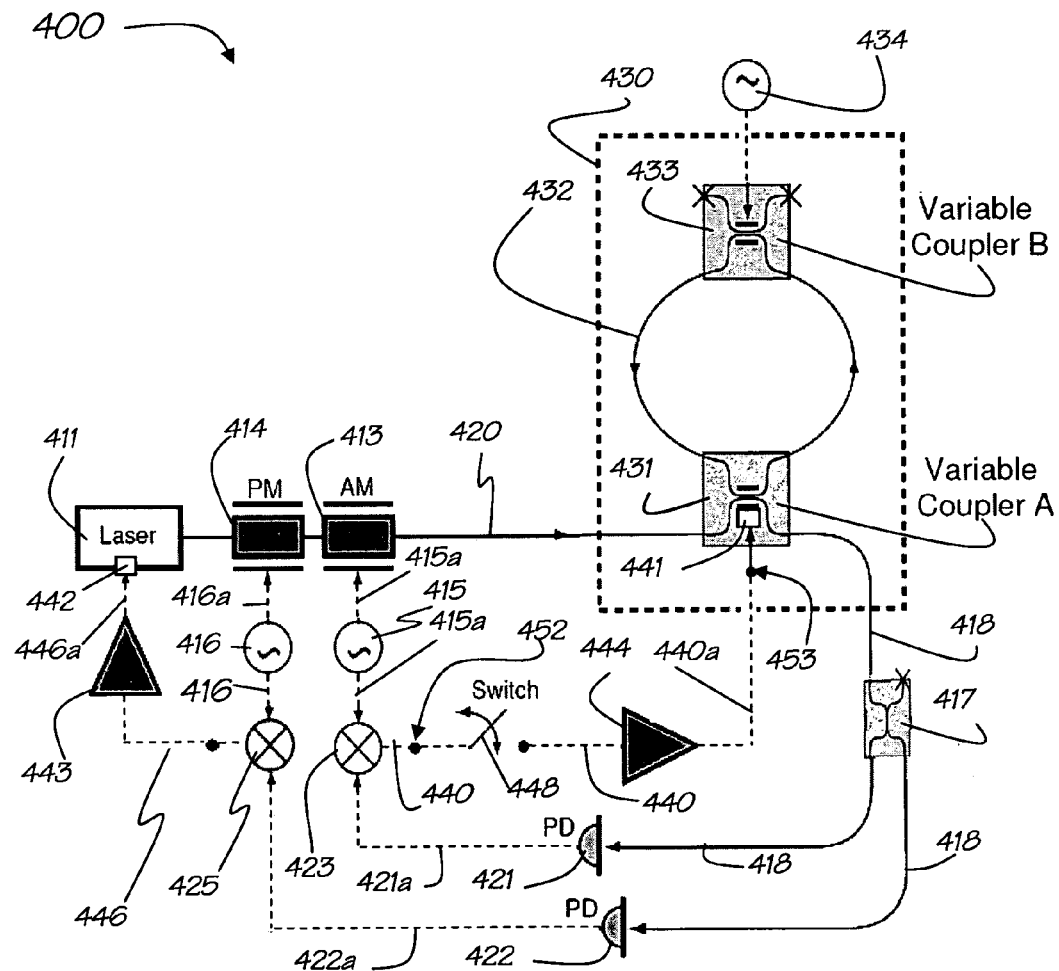
FIG. 10 is a schematic depiction of an optical fibre ring arrangement of an apparatus for carrying out the cavity enhanced amplitude modulated laser absorption spectroscopy method showing both the phase-modulated frequency locking control loop for locking the laser to a cavity resonance and the amplitude modulated impedance matching control loop for monitoring the loss within the resonator cavity.

In a second exemplary arrangement, schematic of a fibre-based ring cavity apparatus 400 for implementing the CEAMLAS method described above is depicted in FIG. 10. The dashed box 430 denotes the resonator cavity which comprises a fibre ring cavity 432 having two optical couplers 431 and 433. In the present arrangement, couplers 431 and 433 use a pair of evanescently coupled fibres whose separation is actuated via a piezoelectric transducer (PZT) to give a variable fibre coupler with coupling ratio from 0 to 1, dependent on the applied voltage to the PZT. Such coupler elements 431 and 433 are available from Canadian Instrumentation and Research, Inc of Ontario, Canada [Product 905(P)/905(P-E]. In the present arrangement, both couplers 431 and 433 are variable couplers (denoted as Variable Couplers A and B respectively) to demonstrate the sensitivity of the system to a loss imparted to the resonator cavity 430 by variable coupler B 433. This loss is to simulate a physical measurement of a loss feature at a particular frequency and is simulated in the present arrangement by a loss function generator 434.

Figure 11A:
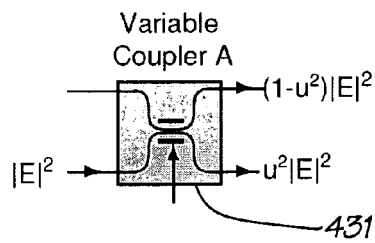
FIGS. 11A and 11B are schematic depictions of the variable reflectivity elements of the resonator cavity of FIG. 10 indicating the relationship of the coupling coefficients u and v used to describe the cavity enhanced amplitude modulated laser absorption spectroscopy method.
Figure 11B:
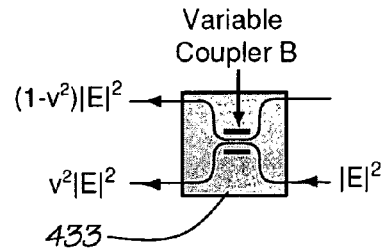

FIGS. 11A and 11B respectively show the relationship of the coupling coefficients u and v described above to the variable couplers A and B (431 and 433 respectively). The Coupler A 431 has variable electric field coupling coefficient u as described above whereas, the variable Coupler B 433 introduces a broadband intracavity loss into the resonator cavity 430, which is associated with the coupling ratio v described above, such that the response of the resonator cavity 430 is as is described in Equation 6. Besides these two couplers, the rest of the cavity is effectively lossless.

As before RF laser modulation interferometry techniques are used to a) lock the laser to resonance using a PDH frequency locking scheme by phase modulating (PM) the output from tunable laser 411 using a suitable optical PM modulator 414 at a modulation frequency of $\omega_{PM}$ (416a generated by signal generator 416); and b) interrogate the impedance coupling condition of the locked resonator cavity 430 by, after the laser is locked to resonance, introducing AM sidebands to the PM-modulated output using a suitable optical AM modulator 413 at an RF frequency, $\omega_{AM}$ (415a generated by signal generator 415), such that $\omega_{AM}$ is well outside the full-width half-maximum (FWHM) of the fibre ring cavity resonance to which the output from laser 411 has been locked.

As before, the light reflected from the variable reflectance coupler 431 is directed via a beamsplitter element 417 to photodetectors 421 and 422 which respectively produce modulated photocurrents 421a and 422a. The AM modulated output 421a from detector 421 is demodulated by demodulator 423 to provide an AM error signal 440 which is fed back in an active negative feedback loop to the actuator 441 (e.g. a PZT element of reflector 431 which acts to vary the distance between the close-coupled optical fibres of coupler 431 thus varying the coupling ratio between the fibres and thus the effective reflectivity of the coupler) of variable input reflector 431 via amplifier 444 to complete the impedance matching loop. Similarly, the PM modulated output 422a from detector 422 is demodulated by demodulator 425 to provide a PM error signal 446 which is directed in an active negative feedback loop to a suitable actuator 442 on the tunable laser source 411 via amplifier 443 to complete the PDH locking loop and thus maintain the carrier frequency of the output from the laser source locked at the particular cavity resonance. For the rest of this discussion, it is assumed that the laser source 411 is actively locked to the resonance of the fibre ring cavity 430 via the PDH locking loop.

The fibre laser source 411 in the present arrangement is a commercial fibre laser at 1550 nm, having a nominal linewidth of 2 kHz and optimum output power of $P_{opt}$~10 mW. The output from the laser was amplitude modulated by an electro-optic modulator 413 at 20 MHz. The responsivity of the AM photodetector 421 was η=1 Amp/Watt. The fibre ring cavity 430 had an initial free-spectral-range (FSR) of ~50 MHz, and a Finesse F ~60, which corresponds to a cavity resonance FWHM of ~0.8 MHz.

Figure 12:
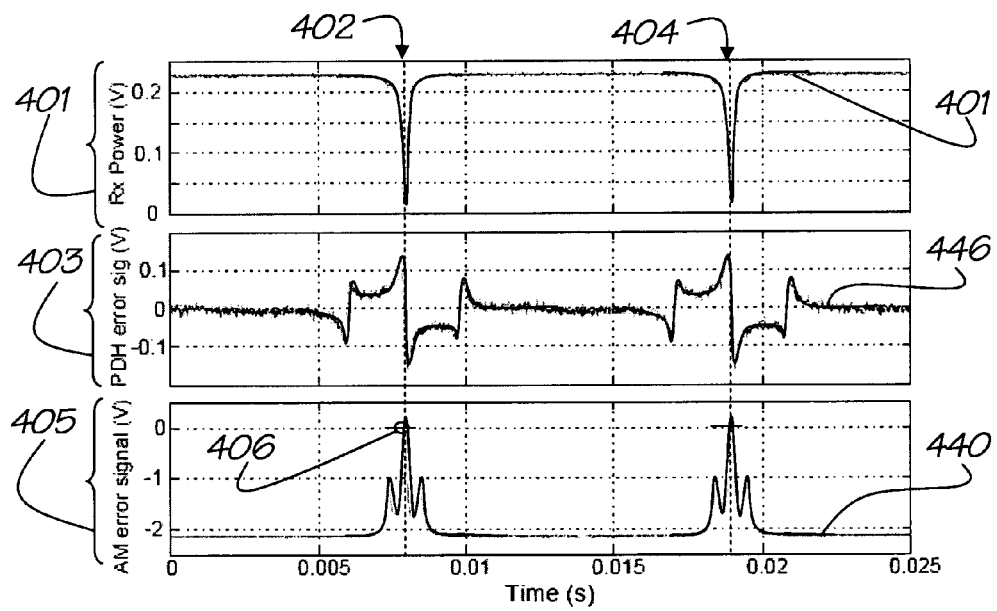
FIG. 12 is a graph showing three plots respectively depicting: top—the reflected power as observed by the photodetector; middle—the PM error signal used for locking the laser frequency to the resonator cavity; and bottom—the AM error signal for impedance matching of the resonator cavity to losses therein, for the fibre arrangement of FIG. 10 as the laser frequency is scanned through two resonances of the cavity.

FIG. 12 shows traces recorded as the laser frequency is scanned across two cavity resonances (corresponding to points 402 and 404 in FIG. 12) with both AM and PM applied to the incident laser beam (420 of FIG. 10) using modulators 413 and 414 respectively. The top trace 401 shows the optical power 418 reflected off the resonator cavity 430 from variable Coupler A (431) and incident on the impedance matching control loop photodetector 421 and observed with an oscilloscope (not shown) before being demodulated with demodulator 423. The free spectral range of the resonator cavity 430 in this particular example is approximately 400 MHz corresponding to a physical length of optical fibre of about 0.5 m within the ring cavity 432. As can be seen from trace 401, the cavity 430 is close to impedance matching and the reflected power drops towards zero on resonance with the cavity resonances at points 402 and 404 (due to the optical power in both the AM and PM sidebands, the reflected power on resonance cannot drop completely to zero). The centre trace 403 shows the characteristic PDH error signal 446 that is derived from the PM sidebands on the carrier laser beam as they interact with the resonances of cavity 430 and detected by locking control loop photodetector 422 and demodulated with demodulator 425 In this particular example, the PM sidebands are at a frequency of 69 MHz.

Figure 13:
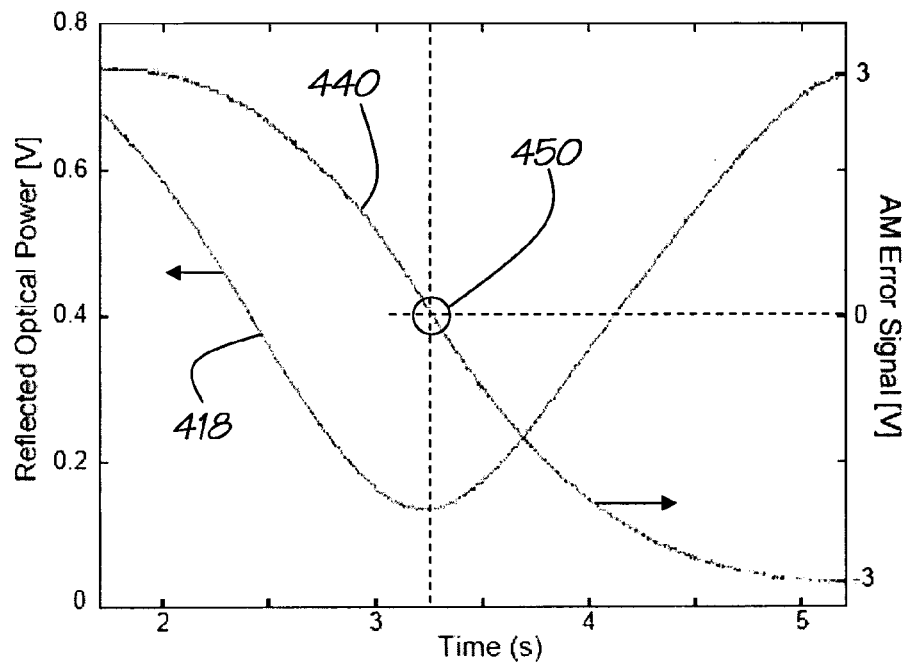
FIG. 13 is graph similar to that of FIG. 1B for the example fibre arrangement of an to apparatus for the cavity enhanced amplitude modulated laser absorption spectroscopy method.

The lower trace 405 of FIG. 12 shows the demodulated AM error signal 440 as the frequency of the incident beam from the tunable laser source 411 is scanned across the resonances of cavity 430. The AM sidebands in the present example are at an offset frequency of 20 MHz with respect to the carrier is frequency $\omega_o$ of the incident beam. As the carrier frequency $\omega_o$ of the laser beam is scanned through the cavity resonances, the AM error signal 440 crosses zero, turns around and once again crosses zero (see at 406). Exactly on resonance, i.e. at points 404 or 406, the error signal 440 is close to zero with a small positive value, indicating that this cavity was marginally over coupled. Once the laser is locked to a particular cavity resonance, the transmission of the input coupler 431 can be scanned while recording both the reflected optical power 418 and the AM error signal 440 to obtain the plot as shown in FIG. 13, with similar characteristics to that of FIG. 1B. As indicated previously, the generation of a graph such as that in FIGS. 1B and 13, demonstrates the significant advantage of the CEAMLAS cavity interrogation technique described above: whilst measuring the reflected optical power 418 yields no first order signal at the impedance matched point 450, the AM error signal 440 reaches it's maximum slope at impedance matched point 450 and yields a large, high sensitivity read out of both cavity impedance and cavity loss as described above.

Figure 14A:
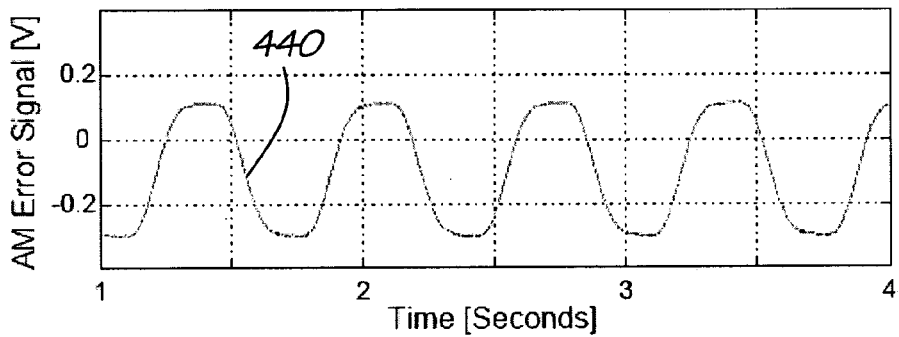
FIGS. 14A and 14B are respectively graphs of the real time AM error signal and the optical power reflected from the resonator cavity of FIG. 10.
Figure 14B:
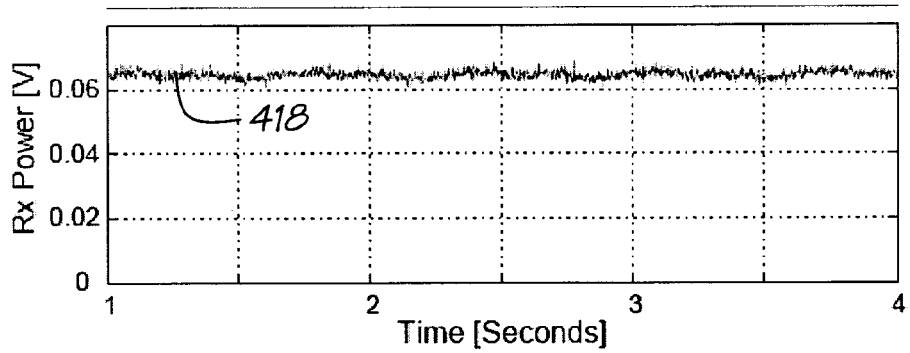

As an example of the capability of the apparatus to measure a loss mechanism associated with the resonator cavity 430, a loss is simulated by the loss signal applied to variable Coupler B (433 of FIG. 10) in the form of a time-varying loss signal at 1.5 Hz. For this measurement the AM error signal 440 was disconnected from the input of the impedance matching amplifier 444 by a switch 448 and the output of amplifier 444 was tuned to adjust the actuator 441 of coupler 431 so that the fibre ring cavity 432 was impedance-matched. The AM error signal 440, measured at the "error point" 452 of FIG. 10, then yielded the real time readout of the total cavity loss including the loss signal imparted by the variable coupler 433. FIG. 14A shows a graph of the resulting AM error signal 440, while FIG. 14B shows a graph of the corresponding optical power 418 from variable Coupler A 431. The AM error signal 440 is seen to yield a large high signal to noise readout of the cavity loss due to the loss signal from variable Coupler B 433. Although the output optical power 418 yields no first order signal, a small, noisy second order signal can just be discerned in FIG. 14B which indicates that this is a less than ideal direct measurement of the optical power for obtaining a measure of the cavity loss in comparison to the large AM error signal 440 signal obtained with the AM modulation method described above To demonstrate the shot noise limited capability of the CEAMLAS method described above and demonstrated in the exemplary examples, the frequency response of the fibre-based apparatus of the second exemplary example is plotted in FIGS. 15A and 15B.

Figure 15A:
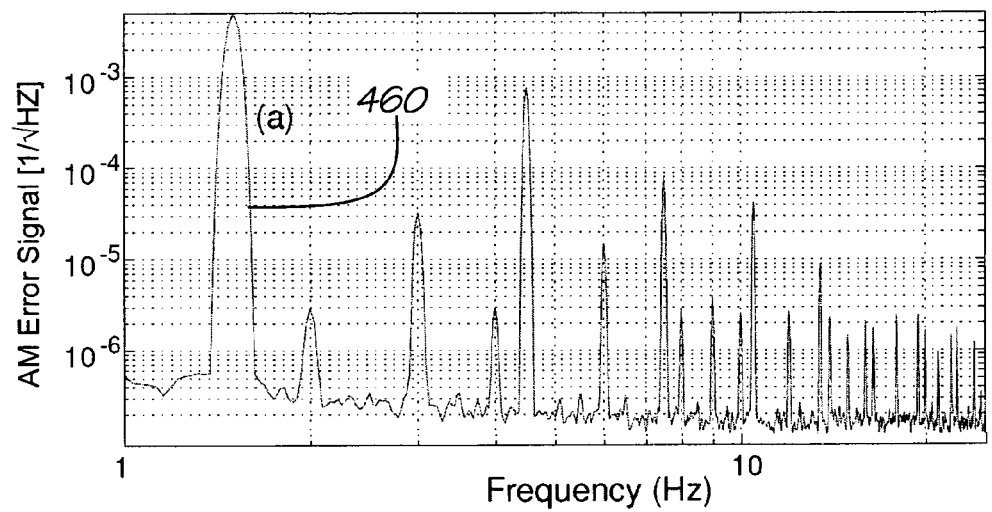
FIG. 15A is a graph of the Fourier transformed loss signal inputted to the resonator cavity of FIG. 10.

Trace 460 of FIG. 15A is a graph of the Fast Fourier Transform (FFT) of the 1.5 Hz AM error signal from variable Coupler B 433 of FIG. 11 (note the higher signal harmonics and the 2 Hz noise components which appeared to be internal to the variable coupler amplifiers used in the apparatus). It was found in this particular arrangement that the limiting noise source of trace 460 was residual frequency noise of the laser source 411. In order to eliminate this noise source, two additional steps were taken:

1) the gain of the amplifier 443 for driving actuator 442 was increased to reduce the residual frequency noise; and 2) the length of the fibre ring cavity 432 was reduced to increase the free-spectral-range (FSR) of the resonator cavity 430 from a value of approximately 50 MHz to approximately 400 MHz, thereby increasing the FWHM to ~6-7 MHz. It will be appreciated that the adjustment of the FSR of the cavity by modifying the cavity length involves a trade-off between mitigating the effects of frequency noise and increasing the interaction length of light within the cavity with the loss mechanism, and that the final FSR decision must consider these factors.

Each of these steps act to minimize residual frequency noise from the stabilised laser source from being coupled into the AM error signal.

Figure 15B:
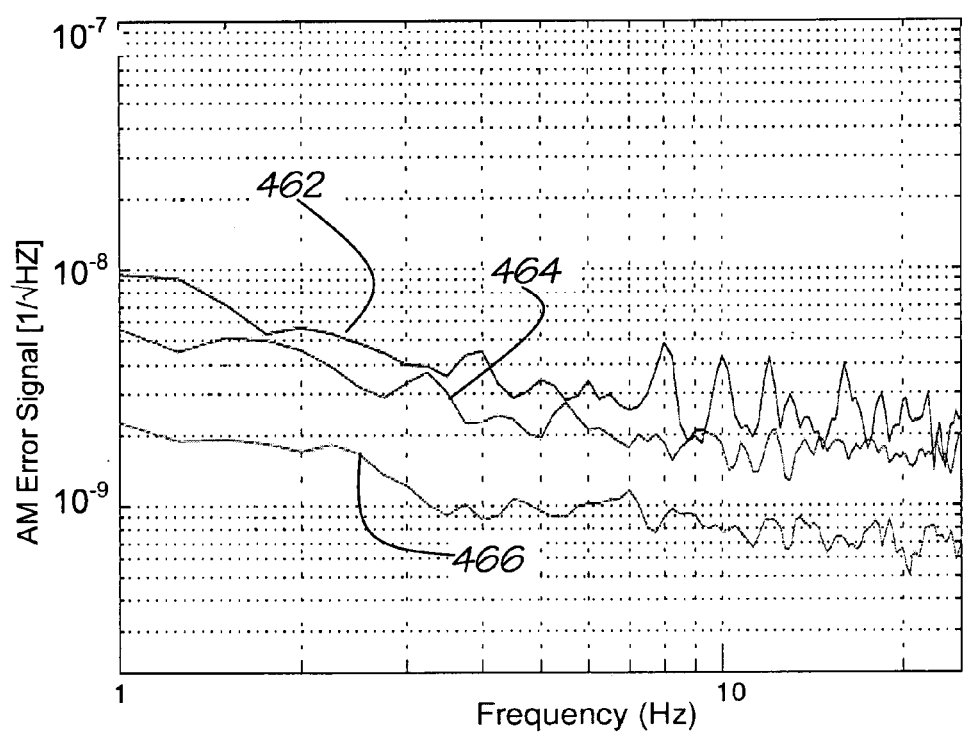
FIG. 15B is a graph showing the absorption sensitivity of the apparatus of FIG. 10 compared with the shot noise and electronic noise limits of the apparatus.

Once these additional steps were taken the sensitivity of the noise floor and the shot noise level for the measurement of the loss signal imparted by variable Coupler B 433 for the shortened fibre ring cavity were measured. Trace 462 of FIG. 15B shows the noise floor demonstrating the absorption sensitivity of the fibre-optic arrangement 400 described above compared with the shot noise level (trace 464). Trace 466 of FIG. 15B is the underlying electronic noise (dark noise) floor of the fibre-optic CEAMLAS arrangement 400.

Using both the time domain trace recorded in FIG. 14A and the AM error signal trace of FIG. 13, the FFT of FIG. 15B has been calibrated in terms of the single pass cavity loss in units of fractions per square root hertz ($/\sqrt{Hz}$). As can be seen from FIG. 15B, the absorption sensitivity 462 is within a factor of 1.5 times or less of the fundamental shot-noise limit for broadband absorption and reaches a sensitivity of $\sim 2\times 10^{-9}/\sqrt{Hz}$, at signal frequencies above ~10 Hz (with experimental parameters Finesse F=60, $P_{opt}$=100 μWatts, λ=1550 nm, η=1 Amp/Watt of the arrangement 400 described above). At lower frequencies 1/f noise within the electronic mixer (demodulator 423 of FIG. 10) would marginally degrade this sensitivity. It should be noted that without cavity enhancement, the detection sensitivity of the fibre-based apparatus 400 would be shot noise limited to $5.6\times 10^{-8}/\sqrt{Hz}$ as given by Equation 1.

Therefore, using the CEAMLAS method, the detection sensitivity of the cavity enhanced loss measurement in the present example using a fibre-based apparatus 400 achieved a sensitivity 28 times better than the single pass limit, demonstrating the significant advantages of the CEAMLAS method to described herein. Furthermore, it is expected that the absorption sensitivity can be significantly improved by increasing cavity finesse, for example to a value in the range of 100 to at least 10,000 or more, or in other arrangements the finesse may be even higher and may be in the range of about 5000 to 50000.

It will be appreciated that the methods/apparatus/devices/systems described/illustrated above at least substantially provide a method and associated apparatus for optical spectroscopy using a cavity enhanced amplitude modulated detection method for shot noise limited detection spectroscopy.

The methods and apparatus described herein, and/or shown in the drawings, are presented by way of example only and are not limiting as to the scope of the invention. Unless otherwise specifically stated, individual aspects and components of the methods and apparatus may be modified, or may have been substituted therefore known equivalents, or as yet unknown substitutes such as may be developed in the future or such as may be found to be acceptable substitutes in the future. The methods and apparatus may also be modified for a variety of applications while remaining within the scope and spirit of the claimed invention, since the range of potential applications is great, and since it is intended that the present methods and apparatus be adaptable to many such variations.

The invention claimed is:

1. A system for spectroscopic detection of a loss in a resonator cavity, the system comprising:

a tunable laser source for generating a laser beam;

a frequency locking system for either locking the frequency of the laser beam to a resonance of the resonator cavity or locking the length of the cavity to the frequency of the laser beam;

a first modulation element comprising an amplitude modulator for modulating the laser beam at a first modulation frequency to generate a modulated laser beam comprising a first modulation signal;

an input coupler adapted for directing the modulated laser beam into the resonator cavity;

a first directing element for directing a first portion of light reflected from the input coupler to a first photodetector to generate a first detected signal; and a first demodulator capable of demodulating the first modulation signal from the first detected signal to generate a first error signal which is a function of the loss in the resonator cavity.

2. A system as claimed in claim 1 wherein the resonator cavity comprises a variable coupler and the system further comprises a first actuator for varying the reflectivity of the variable coupler of the resonator cavity in response to the first error signal to maintain the resonator cavity in an impedance matched state.

3. A system as claimed in claim 2 wherein the variable coupler comprises:
first and second reflectors spaced apart from each other; and
an actuator to vary the position of the first reflector thereby to vary the spacing between the first and second reflectors and thus vary the effective reflectivity of the variable input coupler.

4. A system as claimed in claim 3 wherein the effective reflectivity of the variable input coupler is capable of being varied between about 0% and about 99.99%.

5. A system as claimed in claim 2 wherein the resonator cavity is a guided wave resonator cavity and the variable coupler comprises:
first and second guided wave portions, the first guided wave portion forming part of the resonator cavity and the second guided wave portion in optical communication with the laser source; and
an actuator to vary the optical coupling ratio between the first and second guided wave portions.

6. A system as claimed in claim 5 wherein the optical coupling ratio between the first and second guided wave portions is capable of being varied between about 0% and about 100%.

7. A system as claimed in claim 2 wherein the variable coupler is either a variable frustrated total internal reflection coupler or other variable evanescence wave coupler.

8. A system as claimed in claim 1 wherein either the input or output coupler is the variable coupler.

9. A system as claimed in claim 1 further comprising a detector for detecting the first error signal.

10. A system as claimed in claim 1 wherein the frequency locking system comprises:
a second modulation element for modulating the laser beam at a second modulation frequency such that the modulated laser beam comprises modulated components at both the first and the second modulation frequencies and the detected signal comprises components of both first and second modulation signals;
a second demodulator for demodulating the second modulation signal from the detected signal to generate a second error signal; and
a second actuator for maintaining the frequency of the laser beam at resonance with the cavity in response to the second error signal.

11. A system as claimed in claim 10 wherein the second actuator is adapted for tuning the frequency of the laser beam in response to the second error signal to lock the laser output to a resonance frequency of the cavity.

12. A system as claimed in claim 10 wherein the second actuator is adapted for tuning the length of the resonator cavity in response to the second error signal to lock the cavity resonance to the carrier frequency of the laser output.

13. A system as claimed in claim 10 further comprising a second directing element for directing a second portion of light reflected from the variable input coupler to a second detector to generate a second detected signal wherein the second demodulator is adapted for demodulating the second modulation signal from the second detected signal to generate the second error signal.

14. A system as claimed in claim 10 wherein the second modulator is selected from the group of a phase modulator, a frequency modulator, a current modulator, or a phase modulator which also causes an amplitude modulation.

15. A system as claimed in claim 14 wherein the second error signal is a phase modulated error signal.

16. A system as claimed in claim 14 wherein the phase modulator is an electro-optic modulator.

17. A system as claimed in claim 1 wherein the frequency locking system is a Pound-Drever-Hall frequency locking system.

18. A system as claimed in claim 1 wherein the resonator cavity is a ring cavity.

19. A spectroscopic detection method for detecting of a loss in a resonator cavity, the method comprising:
generating a laser beam using a tunable laser source;
either: locking the frequency of the laser beam to a resonance of the resonator cavity; or
locking the length of the cavity to the frequency of the laser beam;
modulating the laser beam with a first modulation element at a first modulation frequency using amplitude modulation to generate a modulated laser beam comprising a first modulation signal;
directing the modulated laser beam into the resonator cavity via an input coupler;
using a first directing element, directing a first portion of light reflected from the variable input coupler to a first photodetector to generate a first detected signal; and
demodulating the first modulation signal from the first detected signal using a first demodulator to generate a first error signal which is a function of the loss in the resonator cavity.

20. A method as claimed in claim 19 wherein the resonator cavity comprises a variable coupler and the method further comprising the step of:
using a first actuator, varying the reflectivity of the variable coupler in response to the first error signal to maintain the resonator cavity in an impedance matched state.

21. A method as claimed in either claim 19 further comprising the step of:
detecting the first error signal to determine the loss in the resonator cavity at the frequency of the laser.

22. A method as claimed in claim 20 wherein the variable coupler is the input coupler and the method comprises the step of directing the modulated laser beam into the resonator cavity via the variable coupler.

23. A method as claimed in claim 19 wherein the step of locking the frequency of the laser beam to a resonance of the resonator cavity comprises:
modulating the laser beam at a second modulation frequency using a second modulation element such that the modulated beam comprises first and second modulated signals at both the first and the second modulation frequencies and the detected signal comprises components of both the first and the second modulation signals;
demodulating the second modulation signal from the detected signal using a second demodulator to generate a second error signal; and
using a second actuator, maintaining the frequency of the laser beam at resonance with the cavity in response to the second error signal.

24. A method as claimed in claim 23 further comprising the step of directing a second portion of light reflected from the input coupler to a second photodetector to generate a second detected signal and demodulating the second modulation signal from the detected signal using the second demodulator to generate the second error signal.

25. A method as claimed in claim 19 wherein the step of locking the frequency of the laser beam to a resonance of the resonator cavity comprises a Pound-Drever-Hall frequency locking method.

26. A spectroscopic detection method for detecting of a loss in a resonator cavity comprising the steps of:
providing a tunable laser beam;
maintaining the frequency of the laser beam to be on resonance a mode of the resonator;
modulating the laser beam with an amplitude modulation to generate an amplitude modulated laser beam;
resonating the laser beam within the resonator cavity;
detecting reflected amplitude modulated light from the resonator cavity at the frequency of the laser beam; and
generating a loss signal from the amplitude modulated light reflected from the cavity, the loss signal being a function of the loss in the resonator cavity.

* * * * *